US012226432B2

(12) United States Patent
Rotello et al.

(10) Patent No.: US 12,226,432 B2
(45) Date of Patent: Feb. 18, 2025

(54) POLYMER NANOPARTICLE, POLYMER COMPOSITION, METHOD OF MAKING A POLYMER NANOPARTICLE, METHOD FOR TREATMENT OF BACTERIAL BIOFILMS, AND METHOD FOR DETECTION OF BACTERIAL BIOFILMS

(71) Applicant: UNIVERSITY OF MASSACHUSETTS, Boston, MA (US)

(72) Inventors: Vincent M. Rotello, Amherst, MA (US); Ryan Francis Landis, Amherst, MA (US); Akash Gupta, Amherst, MA (US)

(73) Assignee: University of Massachusetts, Boston, MA (US)

( * ) Notice: Subject to any disclaimer, the term of this patent is extended or adjusted under 35 U.S.C. 154(b) by 73 days.

(21) Appl. No.: 17/673,073

(22) Filed: Feb. 16, 2022

(65) Prior Publication Data
US 2022/0184115 A1 Jun. 16, 2022

Related U.S. Application Data

(62) Division of application No. 16/321,859, filed as application No. PCT/US2017/044312 on Jul. 28, 2017, now Pat. No. 11,291,685.

(60) Provisional application No. 62/369,911, filed on Aug. 2, 2016.

(51) Int. Cl.
A61K 31/787 (2006.01)
A01N 43/36 (2006.01)
A01N 43/38 (2006.01)
A01N 43/90 (2006.01)
A61K 9/14 (2006.01)
A61K 9/51 (2006.01)
A61K 38/12 (2006.01)
A61K 45/06 (2006.01)
C08G 61/08 (2006.01)
C08G 61/12 (2006.01)
C12Q 1/04 (2006.01)
G01N 33/569 (2006.01)

(52) U.S. Cl.
CPC ............ *A61K 31/787* (2013.01); *A01N 43/36* (2013.01); *A01N 43/38* (2013.01); *A01N 43/90* (2013.01); *A61K 9/51* (2013.01); *A61K 38/12* (2013.01); *A61K 45/06* (2013.01); *C08G 61/08* (2013.01); *C08G 61/12* (2013.01); *C08G 61/124* (2013.01); *C12Q 1/04* (2013.01); *G01N 33/56911* (2013.01); *A61K 9/14* (2013.01); *C08G 2261/143* (2013.01); *C08G 2261/3324* (2013.01)

(58) Field of Classification Search
CPC ........ A61K 31/787; A61K 9/51; A61K 38/12; A61K 45/06; A61K 9/14; A01N 43/36; A01N 43/38; A01N 43/90; C08G 61/08; C08G 61/12; C08G 61/124; C08G 2261/143; C08G 2261/3324; C12Q 1/04; G01N 33/56911; Y02A 50/30

See application file for complete search history.

(56) References Cited

U.S. PATENT DOCUMENTS

| | | | |
|---|---|---|---|
| 7,915,318 B2 | 3/2011 | Lu et al. | |
| 2003/0177819 A1 | 9/2003 | Maale | |
| 2010/0021391 A1 | 1/2010 | Douglas et al. | |
| 2010/0316643 A1* | 12/2010 | Eckert | A61P 33/02 514/21.3 |
| 2013/0280237 A1 | 10/2013 | Tew et al. | |
| 2014/0045692 A1 | 2/2014 | Rossines et al. | |
| 2015/0025168 A1* | 1/2015 | Lienkamp | A61L 2/232 521/149 |
| 2015/0344639 A1 | 12/2015 | Aamer | |

FOREIGN PATENT DOCUMENTS

WO 2011163637 A2 12/2011

OTHER PUBLICATIONS

Colak et al., "Dual_Functional ROMP-Based Betaines: Effect of Hydrophilicity and Backbone structure on Non fouling Properties", ACS, Langmuir 2012, 28, pp. 666-675.
Costerton et al.; "The Application of Biofilm Science to the Study and Control of Chronic Bacterial Infections." J. Clin. Invest;2003;112:1466-1477.
Costerton et al.; "Biofilm in Implant Infections: Its Production and Regulation.";Int. J. Artif. Organs; 2005;28:1062-1068.

(Continued)

*Primary Examiner* — Sarah Alawadi
*Assistant Examiner* — Thurman Wheeler
(74) *Attorney, Agent, or Firm* — Stites & Harbison, PLLC

(57) ABSTRACT

A polymer nanoparticle includes a polymer having repeating units of formula (I)

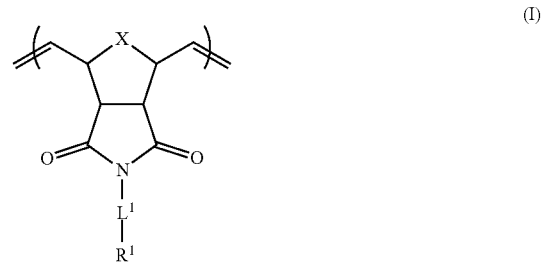

wherein X, L¹, and R¹ are as defined herein. Methods of preparing the polymer nanoparticles and compositions comprising the nanoparticles are also disclosed. The polymers nanoparticles described herein are particularly useful for the treatment of bacterial biofilms.

9 Claims, 12 Drawing Sheets

(56) References Cited

OTHER PUBLICATIONS

Costerton et al.; "Bacterial Biofilms: A Common Cause of Persistent Infections."; Science; 1999; 284: 1318-1322.
Ehrlich et al.; "Mucosal Biofilm Formation on Middle-Ear Mucosa in the Chinchilla Model of Otitis Media." JAMA; 2002;287:1710.
Francolini, I. et al., "Antifouling and antimicrobial biomaterials: an overview", APMIS, vol. 125, 2017; pp. 392-417.
International Search Report for International Application No. PCt/US2017/044312; International Filing Date: Jul. 28, 2017; Date of Mailing Oct. 18, 2017; 8 pages.
James et al.; "Biofilms in Chronic Wounds. Wound Repair Regen." 2007; 16:37-44.
Leng et al., "In Situe Probing the Surface Restructuring of Anitbiofouling Amphiphilic Polybetaines in Water", ACS Macro Letters, 2013, 2, pp. 1011-1015.
Levy et al.; "Antibacterial Resistance Worldwide: Causes, Challenges and Responses." Nat. Med.; 2004; 10:S122-S129.
Lindsay et al., "Bacterial Biofilms within the Clinical Setting: What Healthcare Professionals Should Know." J. Hosp. Infect;2006;64:313-325.
Lynch et al.; "Bacterial and Fungal Biofilm Infections." Annu. Rev. Med.;2008;59:415-428.
Marion-Ferey et al.; "Biofilm Removal from Silicone Tubing: An Assessment of the Efficacy of Dialysis Machine Decontamination Procedures Using an in Vitro Model." J. Hosp. Infect.;2003;53:64-71.
Pichavant et al., "Vancomycin Functionalized Nanoparticles for Bactericidal Biomaterial Surfaces", Biomacrommolecules, Mar. 2016, pp. A-H.
Stewart et al. "Antibiotic Resistance of Bacteria in Biofilms." Lancet; 2001;358;135:138.
Tew et al. "Synthetic Mimic of Antimicrobial Peptide with Nonmembrane-Disrupting Antibacterial Properties", Biomacromolecules 2008, 9, 2980-2983.
Tew et al., Doubly Selective, Antimicrobial Polymers: How Do they Differentiate Between Bacteria? Chem. Eur. J. 2009, 15, 11710.
Tew et al., "Antibacterial and Hemolytic Activities of Quaternanry Pyridinium Functionalized Polynorbornenes", Macromol. Chem. Phys. 2008, 209, 516-524.
Written Opinion of the International Searching Authority for International Application No. PCt/US2017/044312; International Filing Date: Jul. 28, 2017; Date of Mailing Oct. 18, 2017; 6 pages.

\* cited by examiner

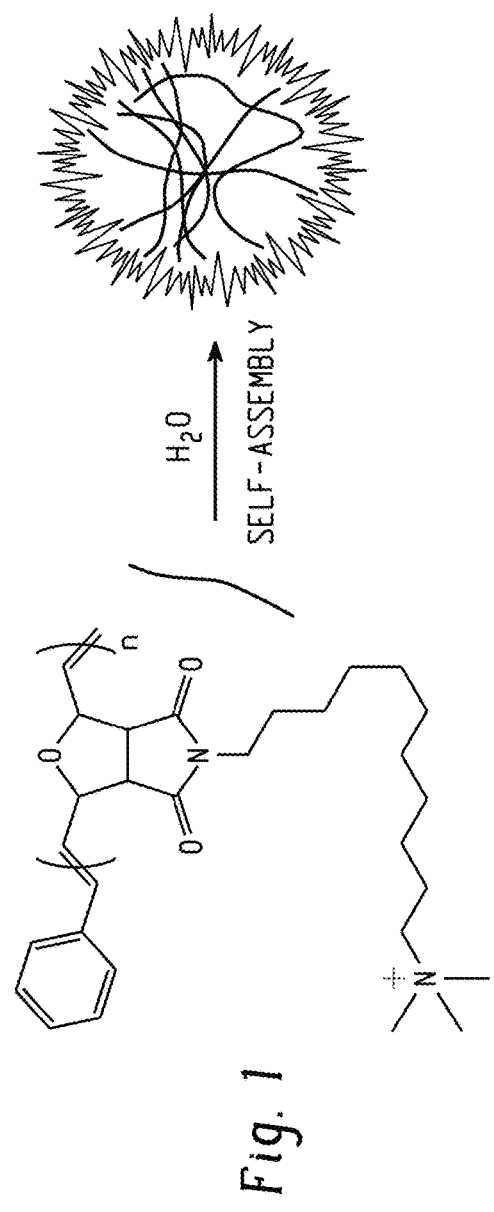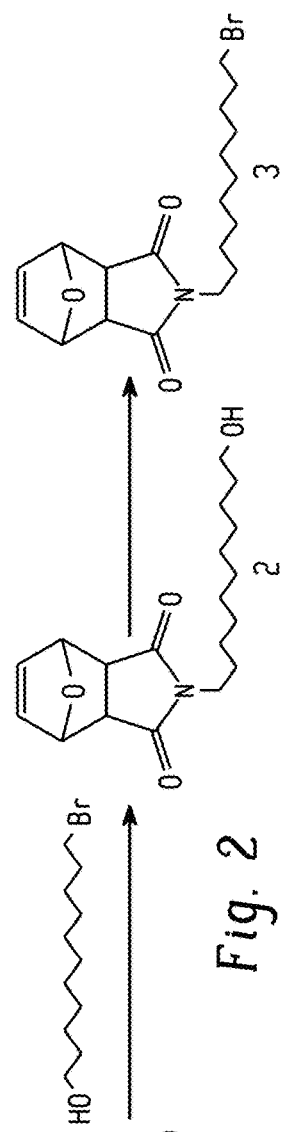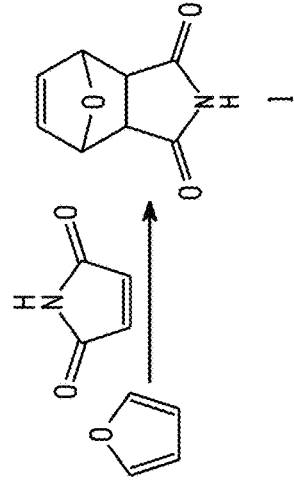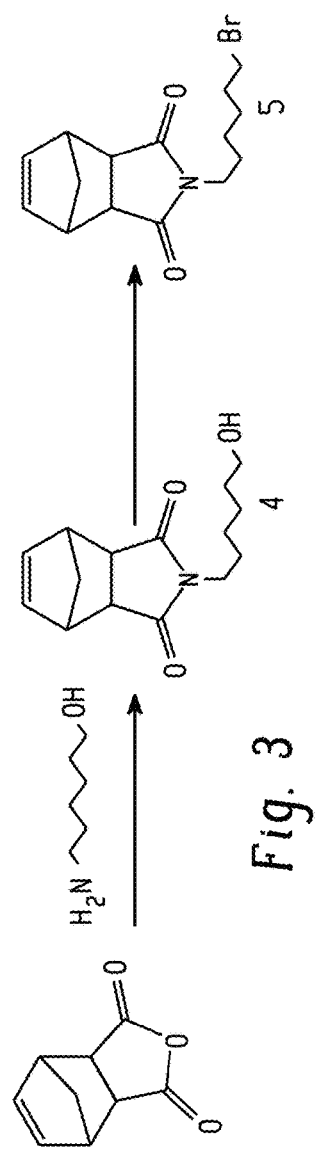
Fig. 1
Fig. 2
Fig. 3

POLYMER NANOPARTICLE, POLYMER COMPOSITION, METHOD OF MAKING A POLYMER NANOPARTICLE, METHOD FOR TREATMENT OF BACTERIAL BIOFILMS, AND METHOD FOR DETECTION OF BACTERIAL BIOFILMS

CROSS REFERENCE TO RELATED APPLICATIONS

This application is a divisional application of U.S. application Ser. No. 16/321,859, filed Jan. 30, 2019, which is a National Stage application of PCT/US2017/044312, filed Jul. 28, 2017, which claims the benefit of U.S. Provisional Application No. 62/369,911, filed Aug. 2, 2016, each of which are incorporated by reference in their entirety herein.

BACKGROUND

Bacterial biofilms are highly resilient microbial assemblies that are difficult to eradicate. See, e.g., Costerton, J. W.; Stewart, P. S.; Greenburg, E. P. Bacterial Biofilms: A Common Cause of Persistent Infections. *Science* 1999, 284, 1318-1322. These robust biofilms frequently occur on synthetic implants and indwelling medical devices including urinary catheters, arthro-prostheses, and dental implants. See, e.g., Lindsay, D.; von Holy, A. Bacterial Biofilms within the Clinical Setting: What Healthcare Professionals Should Know. *J. Hosp. Infect.* 2006, 64, 313-325; Costerto Bacterial biofilms are highly resilient microbial assemblies that are difficult to eradicate. See, e.g., Costerton, J. W.; Stewart, P. S.; Greenburg, E. P. Bacterial Biofilms: A Common Cause of Persistent Infections. *Science* 1999, 284, 1318-1322. These robust biofilms frequently occur on synthetic implants and indwelling medical devices including urinary catheters, arthro-prostheses, and dental implants. See, e.g., Lindsay, D.; von Holy, A. Bacterial Biofilms within the Clinical Setting: What Healthcare Professionals Should Know. *J. Hosp. Infect.* 2006, 64, 313-325; Costerton, J. W.; Montanaro, L.; Arciola, C. R. Biofilm in Implant Infections: Its Production and Regulation. *Int. J. Artif Organs* 2005, 28, 1062-1068; Busscher, H. J.; Rinastiti, M.; Siswomihardjo, W.; van der Mei, H. C. Biofilm Formation on Dental Restorative and Implant Materials. *J. Dent. Res.* 2010, 89, 657-665. Biofilm proliferation can also occur on dead or living tissues, leading to endocarditis, otitis media, and chronic wounds. See, e.g., Costerton, W.; Veeh, R.; Shirtliff, M.; Pasmore, M.; Post, C.; Ehrlich, G. The Application of Biofilm Science to the Study and Control of Chronic Bacterial Infections. *J. Clin. Invest.* 2003, 112, 1466-1477; Ehrlich, G.; Veeh, R.; Wang, X.; Costerton, J. W.; Hayes, J. D.; Hu, F. Z.; Daigle, B. J.; Ehrlich, M. D.; Post, J. C. Mucosal Biofilm Formation on Middle-Ear Mucosa in the Chinchilla Model of Otitis Media. *JAMA* 2002, 287, 1710; James, G. A; Swogger, E.; Wolcott, R.; Pulcini, E. deLancey; Secor, P.; Sestrich, J.; Costerton, J. W.; Stewart, P. S. Biofilms in Chronic Wounds. *Wound Repair Regen.* 2007, 16, 37-44. The persistent infections and their concomitant diseases are challenging to treat, as biofilms develop a high resistance to host immune responses and the extracellular polymeric substances limit antibiotic penetration into biofilms. See, e.g., Stewart, P. S.; Costerton, J. W. Antibiotic Resistance of Bacteria in Biofilms. *Lancet* 2001, 358, 135-138; Szomolay, B.; Klapper, I.; Dockery, J.; Stewart, P. S. Adaptive Responses to Antimicrobial Agents in Biofilms. *Environ. Microbiol.* 2005, 7, 1186-1191. Current techniques to remove biofilms on man-made surfaces include disinfecting the surface with bleach or other caustic agents. See, e.g., Marion-Ferey, K.; Pasmore, M.; Stoodley, P.; Wilson, S.; Husson, G. P.; Costerton, J. W. Biofilm Removal from Silicone Tubing: An Assessment of the Efficacy of Dialysis Machine Decontamination Procedures Using an in Vitro Model. *J. Hosp. Infect.* 2003, 53, 64-71. Biofilms in biomedical contexts are very challenging, with therapies based on excising infected tissues combined with long-term antibiotic therapy, incurring high health care costs and low patient compliance due to the invasive treatment. See, e.g., Lynch, A. S.; Robertson, G. T. Bacterial and Fungal Biofilm Infections. *Annu. Rev. Med.* 2008, 59, 415-428. This issue is exacerbated by the exponential rise in antibiotic resistant bacteria. See, e.g., Levy, S. B.; Marshall, B. Antibacterial Resistance Worldwide: Causes, Challenges and Responses. *Nat. Med.* 2004, 10, S122-S129.

While synthetic materials such as nanoparticles and polymers which exhibit broad spectrum activity against bacterial species exist, lack of specificity and toxicity towards mammalian cells limit their use in biological settings. Accordingly, there remains a continuing need in the art to develop new synthetic platforms which can effectively treat biofilms within a human host without causing adverse side effects such as the hemolysis of red blood cells.

BRIEF SUMMARY

One embodiment is a polymer nanoparticle comprising a polymer comprising repeating units of formula (I)

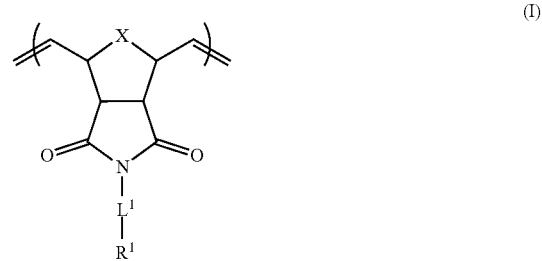

wherein X is independently at each occurrence —O—, —S—, —CH$_2$—, —(CR$^4$R$^5$)—, or

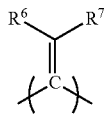

wherein R$^4$ and R$^5$ are independently at each occurrence a C$_{1-6}$ alkyl group and R$^6$ and R$^7$ are independently at each occurrence hydrogen or a C$_{1-6}$ alkyl group; L$^1$ is independently at each occurrence a divalent group that is (—CH$_2$—)$_z$, wherein z is an integer from 3 to 18; and R$^1$ is independently at each occurrence an ammonium group, a phosphonium group, a zwitterionic group, a carboxylate group, a sulfonate group, an alkylene oxide group, or a combination thereof.

Another embodiment is a method of making the polymer nanoparticle, the method comprising combining the polymer comprising repeating units of formula (I) and an aqueous solution.

Another embodiment is a polymer comprising repeating units of formula (I)

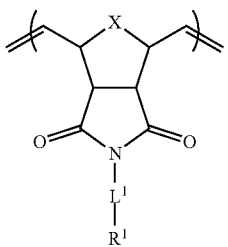

wherein X is independently at each occurrence —O—, —S—, —CH$_2$—, —(CR$^4$R$^5$)—, or

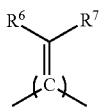

wherein R$^4$ and R$^5$ are independently at each occurrence a C$_{1-6}$ alkyl group and R$^6$ and R$^7$ are independently at each occurrence hydrogen or a C$_{1-6}$ alkyl group; L$^1$ is independently at each occurrence a divalent group that is (—CH$_2$—)$_z$, wherein z is an integer from 3 to 18; and R$^1$ is independently at each occurrence an ammonium group, a phosphonium group, a zwitterionic group, a carboxylate group, a sulfonate group, an alkylene oxide group, or a combination thereof.

Another embodiment is a method of treating a bacterial biofilm, the method comprising contacting an aqueous composition comprising a plurality of polymer nanoparticles or the polymer with a bacterial biofilm.

Another embodiment is a method for detecting a bacterial biofilm, the method comprising contacting an aqueous composition comprising a plurality of polymer nanoparticles comprising a copolymer comprising repeating units of formula (I) and (IX)

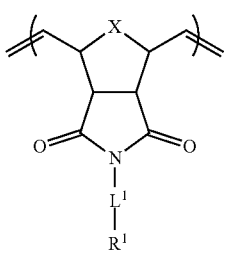

(I)

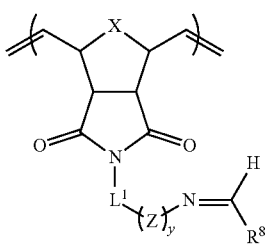

(IX)

wherein X is independently at each occurrence —O—, —S—, —CH$_2$—, —(CR$^4$R$^5$)—, or

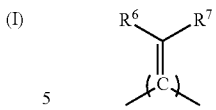

wherein R$^4$ and R$^5$ are independently at each occurrence a C$_{1-6}$ alkyl group and R$^6$ and R$^7$ are independently at each occurrence hydrogen or a C$_{1-6}$ alkyl group; L$^1$ is independently at each occurrence a divalent group that is (—CH$_2$—)$_z$, wherein z is an integer from 3 to 18; R$^1$ is independently at each occurrence an ammonium group, a phosphonium group, a zwitterionic group, a carboxylate group, a sulfonate group, an alkylene oxide group, or a combination thereof; Z is a divalent C$_{6-20}$ arylene group, a divalent C$_{1-20}$ alkylene oxide group, a divalent poly(C$_{1-6}$ alkylene oxide) group, or an amino acid containing group; y is 0 or 1; and R$^8$ is a fluorescent group; with a surface; and measuring fluorescence, wherein the presence of fluorescence is indicative of the presence of a bacterial biofilm.

These and other embodiments are described in detail below.

BRIEF DESCRIPTION OF THE DRAWINGS

The following Figures are exemplary embodiments.

FIG. 1 is a schematic illustration of polymer self-assembly into polymer nanoparticles.

FIG. 2 is a chemical scheme illustrating the synthesis of compounds 1, 2, and 3.

FIG. 3 is a chemical scheme illustrating the synthesis of compounds 4 and 5.

The y-axis is the highest concentration the cells grew in during passaging. FIG. 16 is representative of three independent experiments.

DETAILED DESCRIPTION

Figure 4:
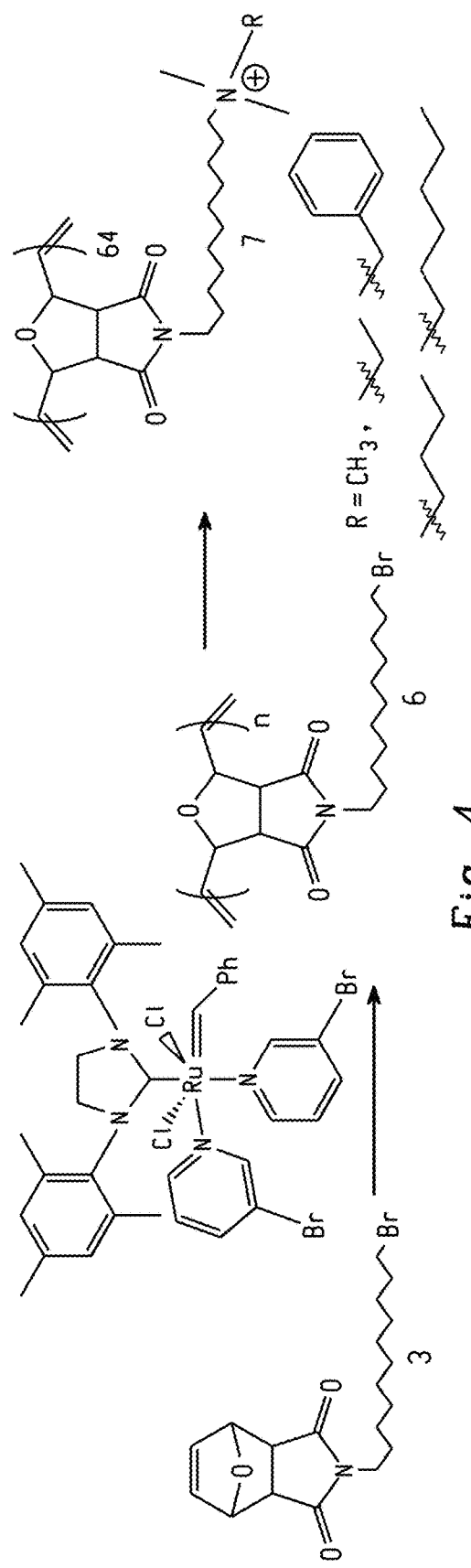
FIG. 4 is a chemical scheme illustrating the synthesis of polymers 6 and 7.

The present inventors have developed a synthetic route to spontaneously generate norbornene-based polymeric nanoparticles in aqueous environments. The strategy described herein involves incorporating homopolymers having long alkyl chains between the norbornene backbones and the terminal headgroups. It is believed that the self-assembly of these polymers into nanoparticles is dictated via the hydrophobic effect, similar to traditional diblock polymeric micelles. Without wishing to be bound by theory, it is believed that the polymers can assemble and bury the long alkyl chains while exposing the charged terminal head group of each repeat unit. The polymer nanoparticles described herein can address the lack of specificity and toxicity towards mammalian cells typical of other known synthetic systems. The polymeric nanoparticles described herein possess low minimal inhibitor concentrations (MICs) in the nanomolar range towards pathogenic planktonic bacteria while maintaining remarkable hemolytic activities. Additionally, the present inventors have demonstrated the effective killing of pathogenic biofilms, not yet observed with other polymer-based systems. The polymeric nanoparticles can eradicate biofilms, while maintaining a high therapeutic index against red blood cells. Advantageously, the polymeric nanoparticles described herein do not require the presence of organic solvents during preparation, and additional purification is also not required, saving both time and money. In addition, consistent nanoparticle size is possible compared to traditional micelle formation strategies. In another advantageous feature, the present inventors have shown that further conjugating a fluorescent dye molecule to the polymer backbone used to form the polymer nanoparticles can be particularly useful for imaging the biofilms, with potential applications for in vivo imaging. Furthermore, the present inventors have also discovered co-incubation of the polymer nanoparticles and an antibiotic can provide a therapeutic synergy, enhancing antibiotic uptake into the biofilms for improved therapeutic efficacy.

Accordingly, one aspect of the present disclosure is a polymer nanoparticle. The polymer nanoparticles can have a diameter of 1 to 100 nanometers, or 1 to 50 nanometers, or 1 to 25, nanometers, or 10 to 20 nanometers. The diameter of the particles can be measured using known techniques, for example, by measuring the diameter observed by transmission electron microscopy (TEM). There is no particular restriction on the shape of the polymer nanoparticles, which can be dictated, for example, by polymer composition, polymer molecular weight, polymer concentration, and the like. In some embodiments, the polymer nanoparticles can be substantially spherical.

The polymer nanoparticles comprise a polymer comprising repeating units of formula (I)

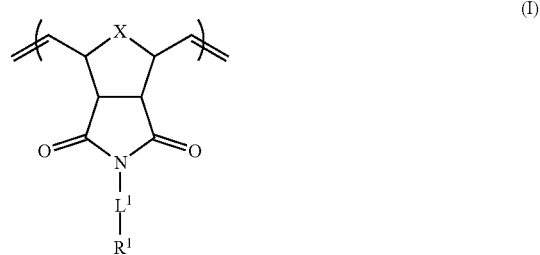

wherein X is independently at each occurrence —O—, —S—, —CH$_2$—, —(CR$^4$R$^5$)—, or

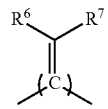

wherein R$^4$ and R$^5$ are independently at each occurrence a C$_{1-6}$ alkyl group and R$^6$ and R$^7$ are independently at each occurrence hydrogen or a C$_{1-6}$ alkyl group; L$^1$ is independently at each occurrence a divalent group that is (—CH$_2$—)$_z$, wherein z is an integer from 3 to 18 (e.g., 3, 4, 5, 6, 7, 8, 9, 10, 11, 12, 13, 14, 15, 16, 17, or 18); and R$^1$ is independently at each occurrence an ammonium group, a phosphonium group, a zwitterionic group, a carboxylate group, a sulfonate group, an alkylene oxide group, or a combination thereof. In some embodiments, the polymer nanoparticle comprises a polymer that is a homopolymer consisting of repeating units of formula (I).

In some embodiments, X in formula (I) can be —O—. In some embodiments, X in formula (I) can be —CH$_2$—. In some embodiments, L$^1$ in formula (I) is a divalent group that is (—CH$_2$—)$_z$, wherein z is an integer from 6 to 12 (e.g., 6, 7, 8, 9, 10, 11, or 12).

As described above, R$^1$ can be an ammonium group, a phosphonium group, a zwitterionic group, a carboxylate group, a sulfonate group, an alkylene oxide group, or a combination thereof. In some embodiments, R$^1$ is an ammonium group. For example, in some embodiments, R$^1$ is an ammonium group of formula (II)

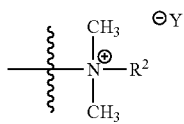

(II)

wherein R² is a $C_{1-12}$ alkyl group or a $C_{7-20}$ alkylaryl group, and Y is bromide, chloride, fluoride, iodide, hydroxide, phosphate, sulfonate, carbonate, acetate, hexafluorophosphate, tetrafluoroborate, mesylate, trifluoroacetate, p-toluenesulfonate, or a combination thereof. In some embodiments, Y is bromide, hydroxide, or a combination thereof. In some embodiments, R² is preferably a $C_{1-12}$ alkyl group, more preferably a $C_{1-6}$ alkyl group, or a benzyl group. For example, the ammonium group can be selected from the following ammonium groups:

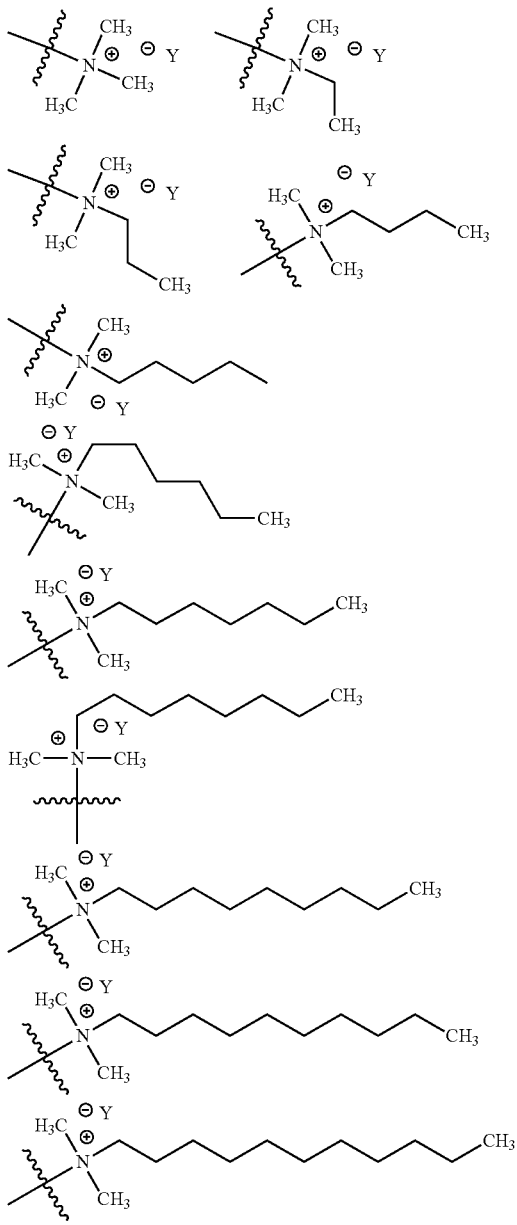

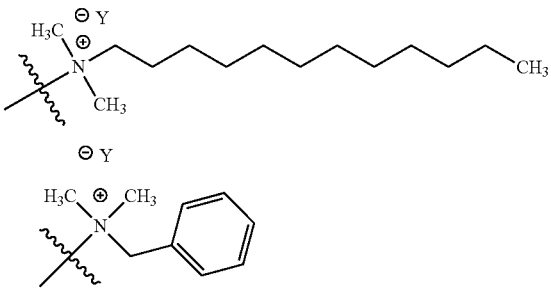

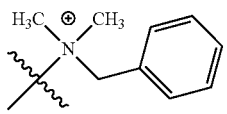

wherein Y is as defined above.

In some embodiments, R¹ can be a phosphonium group, for example, a phosphonium group according to formula (III)

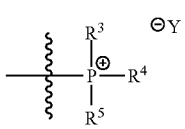

(III)

wherein R³, R⁴, and R⁵ are independently at each occurrence a $C_{1-12}$ alkyl group, a $C_{3-12}$ cycloalkyl group, or a $C_{6-20}$ aryl group, and Y is bromide, chloride, fluoride, iodide, hydroxide, phosphate, sulfonate, carbonate, acetate, hexafluorophosphate, tetrafluoroborate, mesylate, trifluoroacetate, p-toluenesulfonate, or a combination thereof. In some embodiments, Y is bromide, hydroxide, or a combination thereof. R³, R⁴, and R⁵ can be the same or different. In some embodiments, each of R³, R⁴, and R⁵ are a $C_{1-12}$ alkyl group, preferably a $C_{1-6}$ alkyl group, including linear and branched alkyl groups. In some embodiments, each of R³, R⁴, and R⁵ are a $C_{6-12}$ aryl group. For example, the phosphonium group can be selected from the following phosphonium groups:

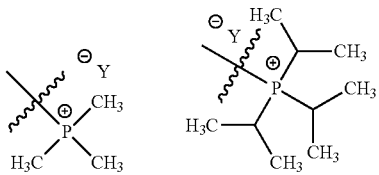

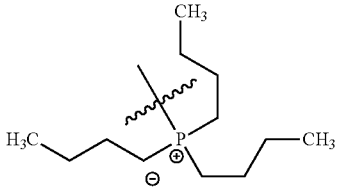

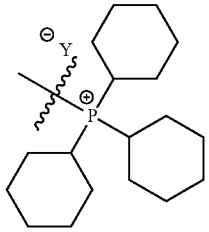 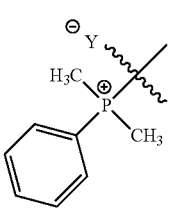

-continued

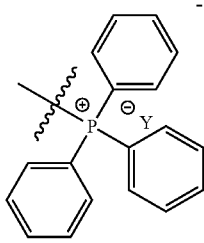

wherein Y is as defined above.

In some embodiments, $R^1$ can be a zwitterionic group. A zwitterionic group is a group of the formula -A-B-C, wherein A is a center of permanent positive charge or a center of permanent negative charge, B is a divalent group comprising a $C_{1-12}$ alkylene group, a $C_{6-30}$ arylene group, or an alkylene oxide group, and C is a center of permanent negative charge or a center of permanent positive charge, provided that the zwitterion has an overall net charge of zero (i.e., the zwitterion is net neutral). For example, in an embodiment wherein A is a center of permanent positive charge, C is a center of permanent negative charge. For example, in an embodiment wherein A is a center of permanent negative charge, C is a center of permanent positive charge. In some embodiments, a center of permanent positive charge can include a quaternary ammonium group, a phosphonium group, a sulfonium group, and the like. In some embodiments, the center of permanent positive charge is preferably an ammonium group. In some embodiments, a center of permanent negative charge can include a sulfonate group, a phosphonate group, a carboxylate group, a thiolate group, and the like. In some embodiments, the zwitterionic group is a sulfobetaine group, a phosphorylcholine group, or a carboxy betaine group. In an embodiment, the zwitterionic group is a sulfobetaine group wherein A is ammonium (e.g., a divalent dimethyl ammonium group ($—N^+(CH_3)_2—$)), B is propylene or butylene, and C is a sulfonate group ($—SO_2O^-$). In an embodiment, the zwitterionic group is a carboxy betaine group wherein A is ammonium (e.g., a divalent dimethyl ammonium group ($—N^+(CH_3)_2—$)), B is methylene or ethylene, and C is a carboxylate group ($—COO^-$). In an embodiments, the zwitterionic grop is a phosphorylcholine group wherein A is a phosphonate, B is ethylene, and C is an ammonium group. For example, the zwitterionic group can be selected from the following zwitterionic groups:

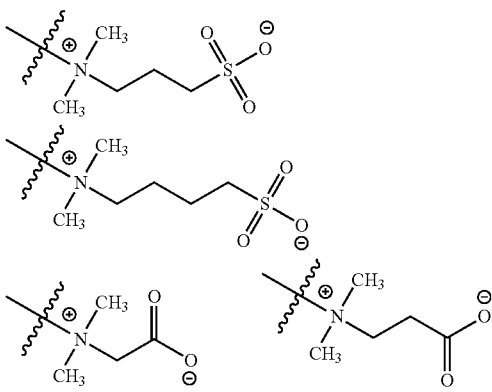

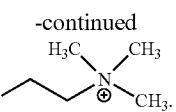

In some embodiments, $R^1$ can be a carboxylate group, for example a carboxylate group of formula (IV)

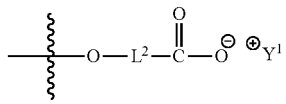

(IV)

wherein $L^2$ is a group comprising a $C_{1-12}$ alkylene group, a $C_{6-30}$ arylene group, or an alkylene oxide group, preferably a $C_{1-12}$ alkylene group, more preferably a $C_{1-6}$ alkylene group. $Y^1$ is a cationic group, for example sodium, potassium, calcium, magnesium, ammonium ($NH_4+$), a quaternary ammonium (e.g., $N(CH_3)_4+$), triethylammonium, diisopropylethylammonium, or a combination thereof.

In some embodiments, $R^1$ can be a sulfonate group, for example, a sulfonate group of formula (V)

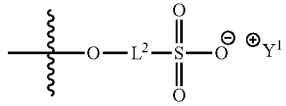

(V)

wherein $L^2$ and $Y^1$ can be as described above for formula (IV).

In some embodiments, $R^1$ can be a group according to formula (VI)

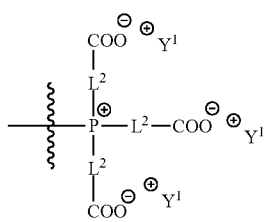

(VI)

wherein $L^2$ and $Y^1$ can be as described above for formula (IV).

In some embodiments, $R^1$ can be an alkylene oxide group or a poly(alkylene oxide) group. For example, $R^1$ can be a group according to formula (VII)

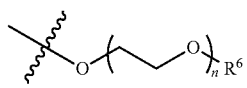

(VII)

wherein $R^6$ is a $C_{1-6}$ alkyl group, preferably a methyl group, or a hydrogen, and n is an integer from 4 to 100.

In some embodiments, $R^1$ is preferably an ammonium group according to formula (II).

In some embodiments, $R^1$ is not a guanidinium group. In some embodiments, $R^1$ is not a pyridinium group. In some embodiments, the polymer excludes repeating units which include one or more guanidinium groups or pyridinium groups.

In some embodiments, the polymer can optionally further comprise repeating units of formula (VIII)

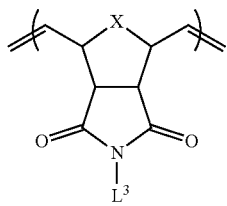
(VIII)

wherein X is independently at each occurrence —O—, —S—, —CH$_2$—, —(CR$^4$R$^5$)—, or

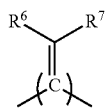

wherein $R^4$ and $R^5$ are independently at each occurrence a $C_{1-6}$ alkyl group and $R^6$ and $R^7$ are independently at each occurrence hydrogen or a $C_{1-6}$ alkyl group; and $L^3$ is independently at each occurrence a $C_{3-20}$ alkyl group. In some embodiments, X in formula (I) can be —O—. In some embodiments, X in formula (I) can be —CH$_2$—. $L^3$ can be a branched or straight chain alkyl group, and can be substituted or unsubstituted. Exemplary $L^3$ alkyl groups can include, for example, n-propyl, n-butyl, n-hexyl, 2-ethylhexyl, 2-hexyldecyl, 2-octyldodecyl, and the like. In some embodiments, $L^3$ is preferably a branched alkyl group. In some embodiments, $L^3$ is preferably 2-ethylhexyl, 2-hexyldecyl, 2-octyldodecyl, and the like, more preferably 2-ethylhexyl.

When present, the polymer can include repeating units of formula (VIII) in an amount of greater than 0 to 25 mole percent, based on the total moles of repeating units in the polymer. For example, the polymer can include repeating units of formula (VIII) in an amount of 1 to 25 mole percent, or 5 to 25 mole percent, or 10 to 25 mole percent, or 10 to 20 mole percent. In some embodiments, the polymer does not include any repeating units according to formula (VIII).

In some embodiments, the polymer further comprises repeating units of formula (IX)

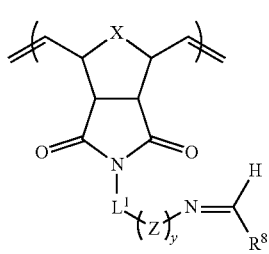
(IX)

wherein X is independently at each occurrence —O—, —S—, —CH$_2$—, —(CR$^4$R$^5$)—, or

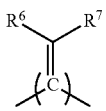

wherein $R^4$ and $R^5$ are independently at each occurrence a $C_{1-6}$ alkyl group and $R^6$ and $R^7$ are independently at each occurrence hydrogen or a $C_{1-6}$ alkyl group; $L^1$ is independently at each occurrence a divalent group that is (—CH$_2$—)$_z$, wherein z is an integer from 3 to 18; Z is a divalent $C_{6-20}$ arylene group, a divalent $C_{1-20}$ alkylene oxide group, a divalent poly($C_{1-6}$ alkylene oxide) group, or an amino acid containing group; y is 0 or 1; and $R^8$ is a fluorescent group. Z and $R^8$ are covalently bonded through a pH sensitive imine linkage. Thus, the group Z is derived from a moiety including a primary amine capable of forming the pH sensitive imine bond to fluorescent dye $R^8$ which includes an aldehyde group. In some embodiments, y is 0, and linking group $L^1$ is directly connected to the fluorescent group $R^8$ via the imine linkage. In other embodiments, y is 1. In some embodiments, Z can be a $C_{6-24}$ monocyclic or polycyclic aromatic group that is substituted with at least one primary amine group. The aromatic group Z can be bonded to linking group $L^1$, for example, through an ether bond. For example, the aromatic group Z can be

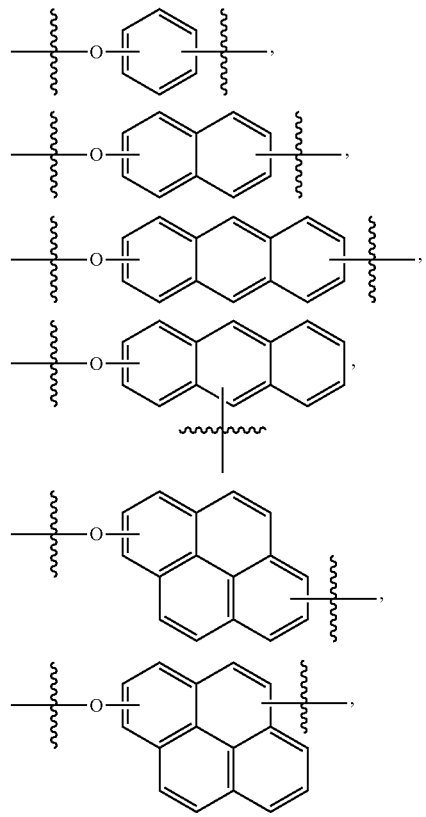

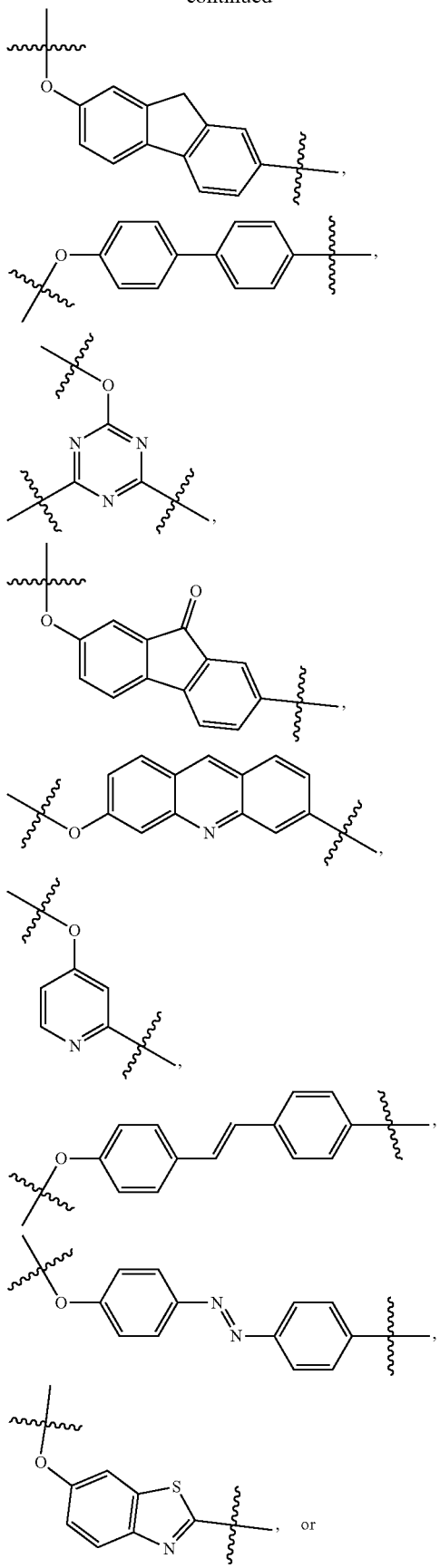

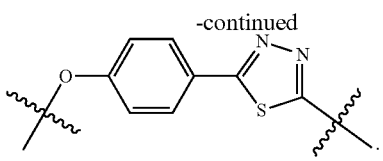

In some embodiments, Z is preferably

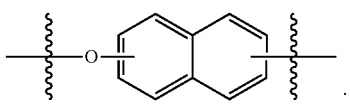

In some embodiments, Z can be an amino acid-containing group, for example, having the structure

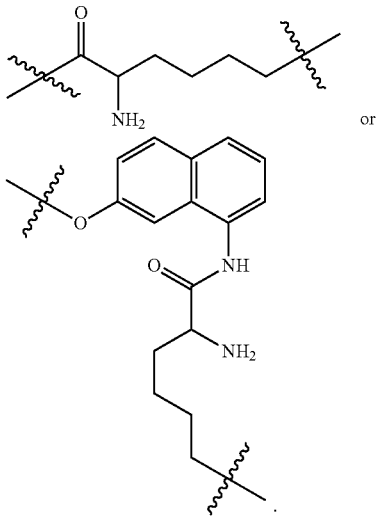

In some embodiments, Z can include a divalent $C_{1-20}$ alkylene oxide group or a divalent poly($C_{1-6}$ alkylene oxide) group, wherein Z is linked to $L^1$ via an ether linkage. Exemplary Z groups of this type can include

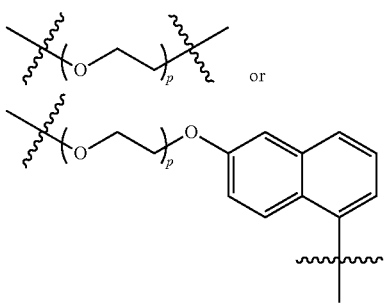

wherein p is an integer from 3 to 10.

The fluorescent dye $R^8$ can generally be any fluorescent dye that includes the functional group as described above needed to form the pH sensitive linkage with group Z, provided that the excitation and emission wavelengths of the dye fall within the region of interest, as can be determined by a person skilled in the art depending on the desired application. In some embodiments, the dye can have an emission in the visible of near-infrared (NIR) spectrum).

Exemplary dyes that can be useful include, but are not limited to, carbocyanine, indocarbocyanine, oxacarbocyanine, thuicarbocyanine and merocyanine, polymethine, coumarine, rhodamine, xanthene, fluorescein, borondipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS. It is noted that the aforementioned dyes can be chemically modified to include an aldehyde group to facilitate conjugation to the polymer, if needed. Such chemical modifications will be apparent to a person skilled in the art. In some embodiments, the dye $R^8$ is preferably a BODIPY dye. BODIPY (borondipyrromethane) dyes have a general structure of 4,4'-difluoro-4-bora-3a,4a-diaza-s-indacene) and sharp fluorescence with high quantum yield and excellent thermal and photochemical stability.

In a very specific embodiment, the polymer further comprises repeating units of formula (IXA)

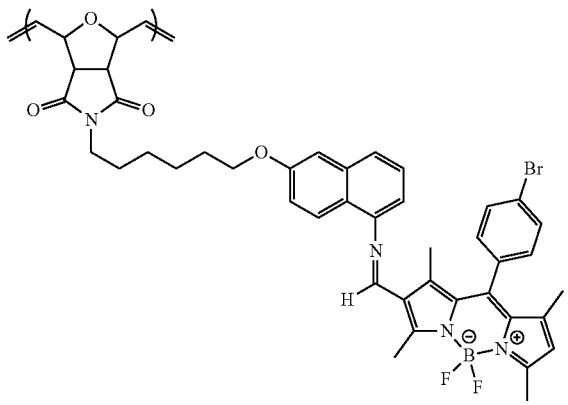

(IXA)

In the above formula IXA, $L^1$ is a $C_6$ methylene group, Z is a linker having the structure and

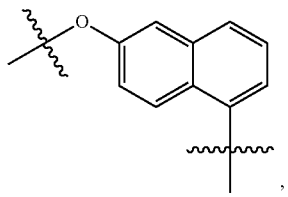 [SMILES: *Oc1ccc2c(*)cccc2c1]

and
$R^8$ is a fluorescent group having the structure

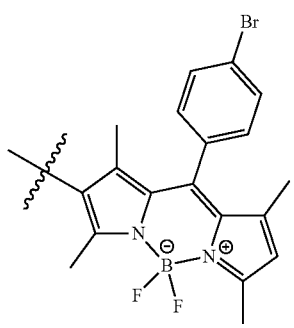

When present, the repeating units of formula (IX) are present in a molar ratio of repeating units of formula (I):repeating units of formula (IX) of 15:1 to 5:1, or 12:1 to 7:1, or 11:1 to 8:1.

In some embodiments, the polymer consists of repeating units according to formula (I), and optionally, formula (VIII) or formula (IX).

In an embodiment, the polymer comprises repeating units according to formula (I), wherein X is —O—, $L^1$ is a divalent group that is $(—CH_2—)_z$, wherein z is an integer from 6 to 12, and $R^1$ is an ammonium group of formula (II), wherein $R^2$ is a $C_{1-6}$ alkyl group or a benzyl group and Y is bromide, hydroxide, or a combination thereof.

In another embodiment, the polymer comprises repeating units according to formula (I), wherein X is —CH$_2$—, $L^1$ is a divalent group that is $(—CH_2—)_z$, wherein z is an integer from 6 to 12, and $R^1$ is an ammonium group of formula (II), wherein $R^2$ is a $C_{1-10}$ alkyl group and Y is bromide, hydroxide, or a combination thereof.

The polymer can have a number average molecular weight of 5,000 to 100,000 grams per mole, or 5,000 to 50,000 grams per mole, or 10,000 to 30,000 grams per mole. Number average molecular weight can be determined using gel permeation chromatography (GPC).

The polymer can generally be prepared using known techniques. For example, the polymer can be prepared by ring opening metathesis polymerization (ROMP) of a suitable cyclic olefin monomer (e.g., an appropriately functionalized norbornene, oxanorbornene, and derivatives thereof) in the presence of a ROMP catalyst such as a ruthenium-containing catalyst. An example of such a procedure is further described in the working examples below. Metal-free ROMP techniques can also be used, for example, as describe in Ogawa, K. A.; Goetz, A. E.; Boydston, A. J. Metal-Free Ring-Opening Metathesis Polymerization. *J. Am. Chem. Soc.* 2015, 137, 1400-1403.

The polymer nanoparticles of the present disclosure can be formed by a method comprising combining the above-described polymer having repeating units according to formula (I) and an aqueous solution. The aqueous solution can comprise water, deionized water, a buffer (e.g., phosphate buffered saline, phosphate buffer, and the like), and the like, or a combination thereof. In some embodiments, the polymer is added to the aqueous solution in an amount of 0.00001 to 10 weight percent, or 0.00001 to 1 weight percent, or 0.0001 to 0.5 weight percent, or 0.0001 to 0.1 weight percent, or 0.0001 to 0.01 weight percent, or 0.0001 to 0.005 weight percent, or 0.0005 to 0.005 weight percent, based on the weight of the aqueous solution to provide the polymer nanoparticles. In some embodiments, the polymer nanoparticles can be provided as a composition in the aqueous solution. In some embodiments, the polymer nanoparticles can be isolated from the aqueous solution following their formation. Isolating the nanoparticles can be by, for example, dialysis, lyophilization, or a combination thereof. Advantageously, the polymer particles can be isolated and stored as a powder, which can be reconstituted in an aqueous solution to provide an aqueous composition comprising the nanoparticle, when desired.

The aqueous composition comprising the nanoparticles can include 0.00001 to 10 weight percent, or 0.00001 to 1 weight percent, or 0.0001 to 0.5 weight percent, or 0.0001 to 0.1 weight percent, or 0.0001 to 0.01 weight percent, or 0.0001 to 0.005 weight percent, or 0.0005 to 0.005 weight percent of the polymer nanoparticles, based on the total weight of the aqueous composition. Accordingly, the aqueous composition can include 90 to 99.99999, such that the amount of the aqueous solution and the polymer nanoparticles totals 100 weight percent.

In some embodiments, the aqueous composition comprising the polymer nanoparticles can optionally further include one or more additives that are generally known in the art, with the proviso that the additives do not significantly adversely affect one or more desired properties of the composition. Furthermore, it can be particularly desirable that the presence of an additive does not significantly interfere with the structure of the nanoparticles. Additives can include stabilizers, thickeners, viscosity enhancers, coloring agent, surfactants, emulsifiers, humectants, antibiotics, siderophores, quorum sensing inhibitors, and the like, or a combination thereof. In some embodiments, no additives are present in the aqueous composition.

In some embodiments, the polymer nanoparticles can optionally further include additives such as hydrophobic antibiotics. The presence of the hydrophobic antibiotic can increase the antimicrobial activity of the nanoparticle. Suitable hydrophobic antibiotics can include nalidixic acid, cinoxacin, norfloxacin, ciprofloxacin, enoxacin, ofloxacin, levofloxacin, sparfloxacin, moxifloxacin, gemifloxacin, trovafloxacin, ampicillin, amoxicillin, carbenicillin, carfecillin, ticarcillin, azlocillin, mezlocillin, piperacillin, cefepime, tetracycline, gentamicin, tobramycin, streptomycin, neomycin, kanamycin, amikacin, cefoselis, and cefquinome. When present, the hydrophobic antibiotic can be included in the nanoparticle in an amount of 0.001 to 10 weight percent, based on the weight of the nanoparticle.

Another aspect of the present disclosure is a method for treating a bacterial biofilm. The method comprises contacting the above described aqueous composition comprising a plurality of the polymer nanoparticles or an aqueous composition comprising the above-described polymer with a bacterial biofilm.

A "biofilm" refers to a population of bacteria attached to an inert or living surface. Thus, biofilms can form on a counter, a table, water pipes, implants, catheters, cardiac pacemakers, prosthetic joints, cerebrospinal fluid shunts, endotracheal tubes, and the like. In some embodiments, the biofilm can be present on a living surface, for example skin or in a wound, and on teeth (e.g., dental plaque). Bacteria in a biofilm are enmeshed in an extracellular polymer matrix, generally a polysaccharide matrix, which holds the bacteria together in a mass, and firmly attaches the bacterial mass to the underlying surface. Evidence has shown that biofilms constitute a significant threat to human health. Wounds and skin lesions are especially susceptible to bacterial infection.

In some embodiments, the bacterial biofilm can be a gram-negative bacterial biofilm or a gram-positive bacterial biofilm. In some embodiments, the bacterial biofilm comprises *Escherichia coli* (e.g., *E. coli* DH5α), *Pseudomonas* bacteria (e.g., *Pseudomonas aeruginosa*), Staphylococcal bacteria (e.g., Staphylococcal *aureus*), Enterobacteriaceae bacteria (e.g., *E. cloacae* complex), *Streptococcus* bacteria, *Haemophilus influenzae*, *Leptospira interrogans*, *Legionella* bacteria, *Micrococcus* bacteria (e.g., *Micrococcus luteus*), *Bacillus* bacteria (e.g., *Bacillus subtilis, Bacillus cereus, Bacillus licheniformic, Bacillus megaterium*), *Burkholderia* bacteria (e.g., *Burkholderia cepacia*), *Amycolatopsis* bacteria (e.g., *Amycolatopsis azurea*), *Mycobacterium* bacteria (e.g., *Mycobacterium tuberculosis*), *Acinetobacter* bacteria (e.g., *Acinetobacter baumannii*), *Enterococcus* bacteria (e.g., *Enterococcus faecium*), *Klebsiella* bacteria (e.g., *Klebsiella pneumonia*), *Acinetobacter* bacteria, or a combination thereof.

Contacting an aqueous composition comprising the nanoparticles or the polymer with a biofilm can effectively kill bacterial cells present in the biofilm. Thus, compositions prepared from the above-described nanoparticles and polymers can be particularly useful as disinfectants or antimicrobial compositions. The contacting can be under conditions effective to treat the biofilm, for example for a time of 10 minutes to 5 hours, or 1 hour to 3 hours, and at a temperature of 25 to 37° C. As used herein, "treating a biofilm" can refer to killing at least 20%, or at least 40%, or at leat 50%, or at least 60%, or at least 80%, or at least 90% of the bacterial cells present in the biofilm. In some embodiments, contacting the composition with a biofilm can completely remove the biofilm (i.e., the dispersion is toxic to greater than 90%, or 99% or 99.9% of the bacterial cells of the biofilm upon contacting the composition with the biofilm).

In some embodiments, the method can further comprise contacting an antibiotic with the bacterial biofilm. Contacting the antibiotic with the bacterial biofilm can occur prior to, simultaneously with, or after contacting the bacterial biofilm with the aqueous composition comprising the polymer nanoparticles. Preferably, contacting the antibiotic with the bacterial biofilm can occur simultaneously with the contacting of the aqueous composition with the bacterial biofilm (i.e., the polymer nanoparticles and the antibiotic can be co-incubated with the bacterial biofilm). The antibiotic can be in addition to any antibiotic that can be present in the polymer nanoparticle formulation as described above. The antibiotic can be a hydrophilic antibiotic, for example, an aminoglycoside, a beta-lactam, a glycopeptide, colistin, and the like, or a combination thereof. In a specific embodiment, the antibiotic can be colistin. Without wishing to be bound by theory, the contacting of a bacterial biofilm with both the polymer nanoparticles and an antibiotic (e.g., colistin) is believed to provide enhance treatment of the bacterial biofilm via a synergistic effect resulting from the co-delivery, as will be discussed further in the working examples below.

Another aspect of the present disclosure is a method for detecting a bacterial biofilm. The method comprises contacting an aqueous composition comprising a plurality of polymer nanoparticles comprising a copolymer comprising repeating units of formula (I) and (IX), as described above, with a surface. The aqueous composition can be as described above in relation to the method for treating a bacterial biofilm. The surface can be, for example, a counter, a table, water pipes, implants, catheters, cardiac pacemakers, prosthetic joints, cerebrospinal fluid shunts, endotracheal tubes, and the like. In some embodiments, the surface can be a living surface, for example skin, a wound, or teeth. The method further comprises measuring fluorescence of the treated surface, where the presence of fluorescence is indicative of the presence of a bacterial biofilm on the surface. In some embodiments, the method can further be a method for treating the detected bacterial biofilm, as contacting the aqueous composition with an infected surface can effectively kill bacterial cells present in the biofilm.

In summary, the present disclosure provides new polymers and polymer nanoparticles prepared therefrom. The polymer nanoparticles demonstrate highly effective therapeutic behavior, successfully eradicating pathogenic biofilm strains of clinical isolates. Thus, the nanoparticles described herein have potential applications as general surface disinfectants as well as antiseptics for wound treatment. The facile self-assembly strategy used to prepare the nanoparticles provides a promising platform to create effective delivery vehicles to combat bacterial biofilms. Furthermore, the therapeutic efficacy of the polymer nanoparticles against bacterial biofilms can be enhanced by co-delivery with an antibiotic.

The polymers, polymer nanoparticles, and methods described herein are further illustrated by the following non-limiting examples.

EXAMPLES

Experimental details for the preparation of the monomers, polymers, and nanoparticles used for the following examples are provided below.

Monomer Synthesis

Compound 1, shown in FIG. 2, was synthesized according to the following procedure. In a pressure tube, furan (4.5 milliliters, 61.7 millimoles, 1.5 eq.) and maleimide (4.0 grams, 41.1 millimoles, 1.0 eq.) were added to 5 milliliters of diethyl ether. The tube was sealed and heated at 100° C. overnight. The pressure tube was then cooled to room temperature and the formed solid was removed by filtration, and washed with copious amounts of diethyl ether to isolate 1 as a white solid. Compound 1 was used without further purification. Proton nuclear magnetic resonance spectroscopy ($^1$H NMR) was used to confirm the structure of compound 1. $^1$H NMR was conducted at 400 MHz using deuterated methanol (MeOD) as the solvent. The chemical shifts are reported as parts per million (ppm) using tetramethylsilane (TMS) as a reference: 11.14 (s, 1H), 6.52 (s, 2H), 5.12 (s, 2H), 2.85 (s, 2H).

Compound 2, shown in FIG. 2, was synthesized according to the following procedure. To a 250 milliliter round bottom flask equipped with a stir bar was added 60 milliliters of dimethyl formamide (DMF). Compound 1 (3.76 grams, 22.7 millimoles, 1.0 eq.) was then added with potassium carbonate (12.59 grams, 91.1 millimoles, 4.0 eq.). The reaction mixture was heated at 50° C. for five minutes. Potassium iodide (0.68 grams, 4.5 millimoles, 0.2 eq.) and 11-bromoundecanol (6.00 grams, 23.9 millimoles, 1.05 eq.) were added and the mixture was stirred at 50° C. overnight. The reaction mixture was subsequently cooled to room temperature, diluted to 150 milliliters with ethyl acetate, and washed with water (7×50 milliliters) and brine (1×50 milliliters). The organic layer was dried with sodium sulfate, filtered, and concentrated by rotary evaporation to yield Compound 2. Compound 2 was purified by sonication of the solid in hexanes, followed by filtration. $^1$H NMR was conducted at 400 MHz using deuterated chloroform (CDCl$_3$) as the solvent. $^1$H NMR (400 MHz, CDCl$_3$) 6.44 (s, 2H), 5.19 (s, 2H), 3.55, (t, 2H), 3.49 (t, 2H), 2.79 (s, 2H), 1.9 (s, 1H), 1.39 (m, 4H), 1.2 (m, 14H).

Compound 3, shown in FIG. 2, was synthesized according to the following procedure. To a 250 milliliter round bottom flask equipped with a stir bar was added compound 2 (2.64 grams, 7.87 millimoles, 1.0 eq.). Dichloromethane (DCM) (100 milliliters) was then added, with tetrabromomethane (3.13 grams, 9.44 millimoles, 1.2 eq.). The reaction was cooled to 0° C. using an ice bath. Finally, triphenylphosphine was added in portions (2.47 grams, 9.44 millimoles, 1.2 eq.) and allowed to stir for three hours. The reaction mixture was then concentrated by rotary evaporation and ethyl ether was added (200 milliliters) and placed in the freezer for 2 hours to precipitate out triphenylphosphine oxide byproduct. The mixture was filtered and the filtrate was concentrated by rotary evaporation. Column chromatography was performed to yield compound 3, as a white solid. $^1$H NMR (400 MHz, CDCl$_3$) 6.51 (s, 2H), 5.27 (s, 2H), 3.45 (t, 2H), 3.41 (t, 2H), 2.83 (s, 2H), 1.85 (q, 2H), 1.55 (q, 2H), 1.41 (q, 2H), 1.29 (m, 12H).

Compound 4, shown in FIG. 3, was synthesized according to the following procedure. To a 500 milliliter round bottom flask equipped with a stir bar was added cis-5-Norbornene-endo-2,3-dicarboxylic anhydride (12.0 grams, 73.1 millimoles, 1.0 eq.). Next, toluene was added (250 milliliters). Finally, 6-amino-1-hexanol (9.0 grams, 76.8 millimoles, 1.05 eq.) was added and the reaction was stirred at reflux using a dean-stark trap overnight. Afterwards, the reaction mixture was concentrated by rotary evaporation, and the residue was dissolved into ethyl acetate (100 milliliters). The ethyl acetate was extracted using 1 Molar hydrochloric acid (HCl) (50 millliters) followed by brine (50 milliliters). The organic layer was and dried, filtered, and concentrated by rotary evaporation to yield compound 4. No further purification was performed. $^1$H NMR (400 MHz, CDCl$_3$) 6.07 (s, 2H), 3.6 (t, 2H), 3.35 (br, 2H), 3.29 (t, 2H), 3.21 (br, 2H), 1.7 (t, 2H), 1.51 (m, 3H), 1.4 (m, 2H), 1.31 (m, 2H), 1.22 (m, 2H).

Compound 5, shown in FIG. 3, was synthesized according to the following procedure. To a 250 millliter round bottom flask equipped with a stir bar was added 4 (5.0 grams, 19.0 millimoles, 1.0 eq.). Next, DCM (100 milliliters) was added along with tetrabromomethane (7.87 grams, 23.75 millimoles, 1.25 eq.). The reaction was cooled to 0° C. using an ice bath. Finally, triphenylphosphine was added in portions (7.48 grams, 28.5 millimoles, 1.50 eq.) and allowed to stir for three hours. Afterwards, the reaction mixture was concentrated by rotary evaporation and ethyl ether was added (200 milliliters) and placed in the freezer for 2 hours to precipitate out triphenylphosphine oxide byproduct. The reaction mixture was filtered and the filtrate was concentrated by rotary evaporation. Column chromatography was performed to yield 5, a light yellow oil. $^1$H NMR (400 MHz, CDCl$_3$) 6.1 (s, 2H), 3.39 (t, 2H), 3.38 (s, 2H), 3.31 (t, 2H), 3.25 (s, 2H), 1.83 (q, 2H), 1.72 (d, 1H), 1.54 (d, 1H), 1.44 (m, 4H), 1.28 (m, 2H).

Polymer Synthesis

Polymer 6, shown in FIG. 4, was synthesized according to the following procedure. To a 10 milliliter pear-shaped air-free flask equipped with a stir bar was added 3 (800 milligrams, 2.0 millimoles, 1.0 eq.) and 4 milliliters of DCM. In a separate 10 milliliter pear-shaped air-free flask was added Grubbs 3$^{rd}$ generation catalyst (35.4 milligrams, 0.04 millimoles, 0.02 eq.) and 1 milliliter of DCM. Both flasks were sealed with septa and attached to a schlenk nitrogen/vaccum line. Both flasks were freeze-pump-thawed three times each. After thawing, Grubbs 3$^{rd}$ generation catalyst was syringed out and quickly added to the flask containing 3 and allowed to react for 10 minutes. After the allotted time, ethyl vinyl ether (200 microliters) was added and allowed to stir for 15 minutes. Afterwards, the reaction was diluted to two times the volume and precipitated into a heavily stirred solution of hexane (300 milliliters). The precipitated polymer was filtered and dissolved into tetrahydrofuran (THF). The polymer was precipitated again into hexane and filtered to yield 6. The polymer molecular weight was characterized by gel permeation chromatography (GPC) against polystyrene standards eluting with tetrahydrofuran. Polymer 6 was found to have a weight average molecular weight (Mw) of 25,698 grams per mole, and a polydispersity (PDI) of 1.04. The polymer was also characterized using $^1$H NMR spectroscopy. $^1$H NMR (400 MHz, CDCl$_3$) 6.0 (br, 1H), 5.7 (br, 1H), 4.95 (br, 1H), 4.4 (br, 1H), 3.4 (br, 2H), 3.25 (br, 2H), 1.79 (q, 2H), 1.5 (br, 2H), 1.34 (br, 2H), 1.2 (br, 14H).

Quaternary ammonium-containing polymer 7, shown in FIG. 4, was synthesized according to the following procedure. Polymer 6 (50 milligrams) was added to a 20 milliliter vial equipped with a stir bar. Next, excess of the necessary tertiary amines was added (10 milliliters of a 1 Molar trimethylamine solution in THF, all other amines were added in an amount of 200 milligrams) to the vial and purged with nitrogen. First stage of the reactions involved stirring for 30 minutes at 80° C. The polymers precipitated during this time. Approximately half of the THF was evaporated and replaced with methanol which re-dissolved the polymers. The reaction was allowed to proceed overnight at 50° C. Afterwards, the solvent was completely evaporated, washed with hexane 2 times, and dissolved into a minimal amount of water. The polymers were added to 10,000 molecular weight cut off (MWCO) dialysis membranes and allowed to stir for 3 days, changing the water periodically. The polymer solutions were filtered through PES syringe filters, and freeze-dried to yield the respective quaternary ammonium polymers 7. NMR indicated complete conversion into the quaternary ammonium salts.

Figure 5:
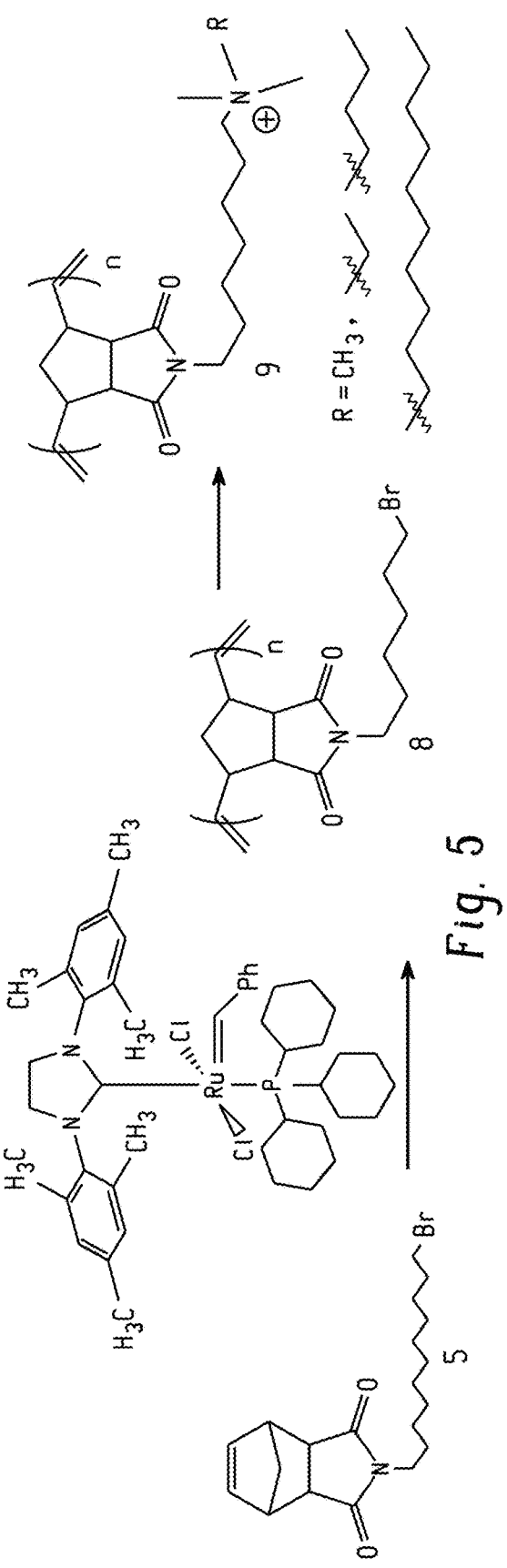
FIG. 5 is a chemical scheme illustrating the synthesis of polymers 8 and 9.

Polymer 8, shown in FIG. 5, was synthesized according to the following procedure. To a 10 milliliter pear-shaped air-free flask equipped with a stirbar was added compound 5 (800 milligrams, 2.46 millimoles, 1.0 eq.) and 5 milliliters of DCM. In a separate 10 milliliter pear-shaped air-free flask was added Grubbs $2^{nd}$ generation catalyst (20 milligrams, 0.047 millimoles, 0.02 eq.) and 1 milliliter of DCM. Both flasks were sealed with septa and attached to a schlenk nitrogen/vacuum line. Both flasks were freeze-pump-thawed three times. After thawing, Grubbs $2^{nd}$ generation catalyst was syringed out and quickly added to the flask containing 5 and allowed to react for 10 minutes. After the allotted time, ethyl vinyl ether (200 microliters) was added and allowed to stir for 15 minutes. The reaction was then diluted to two times the volume and precipitated into a heavily stirred solution of hexane (300 milliliters). The precipitated polymer was filtered and dissolved into THF. The polymer was precipitated again into hexane and filtered to yield polymer 8. Polymer 8 was found to have a Mw of 17,027 grams per mole and a polydispersity of 1.36, as determined by GPC, eluting with THF, and using a polystyrene calibration curve. $^1$H NMR (400 MHz, CDCl$_3$) 5.7 (br, 1H), 5.6 (br, 1H), 3.48 (br, 2H), 3.39 (br, 2H), 3.2 (br, 2H), 2.95 (br, 2H), 1.85 (br, 2H), 1.55 (br, 2H), 1.45 (br, 6H).

Quaternary ammonium-containing polymer 9, shown in FIG. 5, was synthesized according to the following procedure. Polymer 8 (50 mg) was added to 20 ml vials equipped with a stir bar. Next, excess of the necessary tertiary amines was added (10 ml of a 1M trimethylamine solution in THF, all other amines were 200 mg) to the vial and purged with nitrogen. First stage of the reactions involved stirring for 30 minutes at 80° C. The polymers precipitated during this time. Half of the THF was evaporated and replaced with methanol which re-dissolved the polymers. The reaction was allowed to proceed overnight at 50° C. Afterwards, the solvent was completely evaporated, washed with hexane 2 times, and dissolved into a minimal amount of water. The polymers were added to 10,000 MWCO dialysis membranes and allowed to stir for 3 days, changing the water periodically. The polymers were filtered through PES syringe filters, and freeze-dried to yield the respective quaternary ammonium polymers 9. NMR indicated complete conversion into the quaternary ammonium salts.

Polymer Nanoparticle Formation

Figure 7:
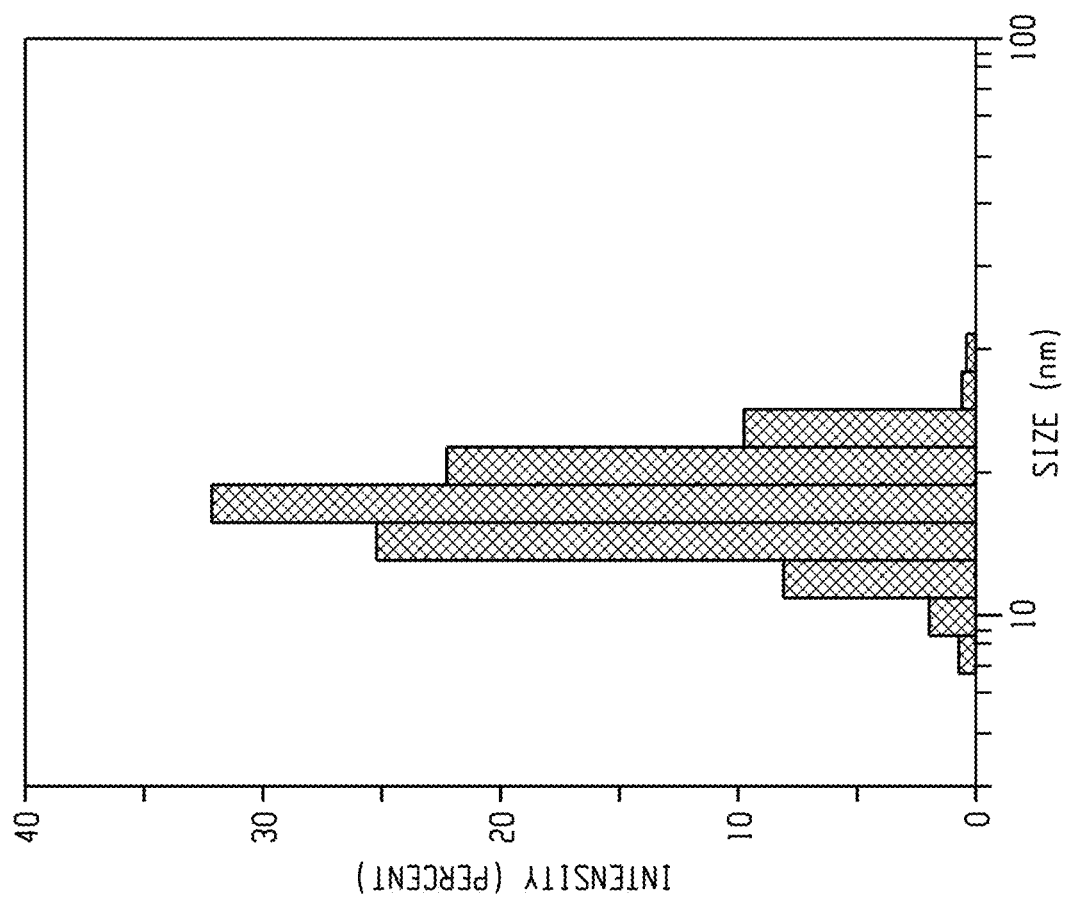
FIG. 7 shows a particle size distribution of the polymer nanoparticles obtained by dynamic light scattering (DLS).
Figure 6:
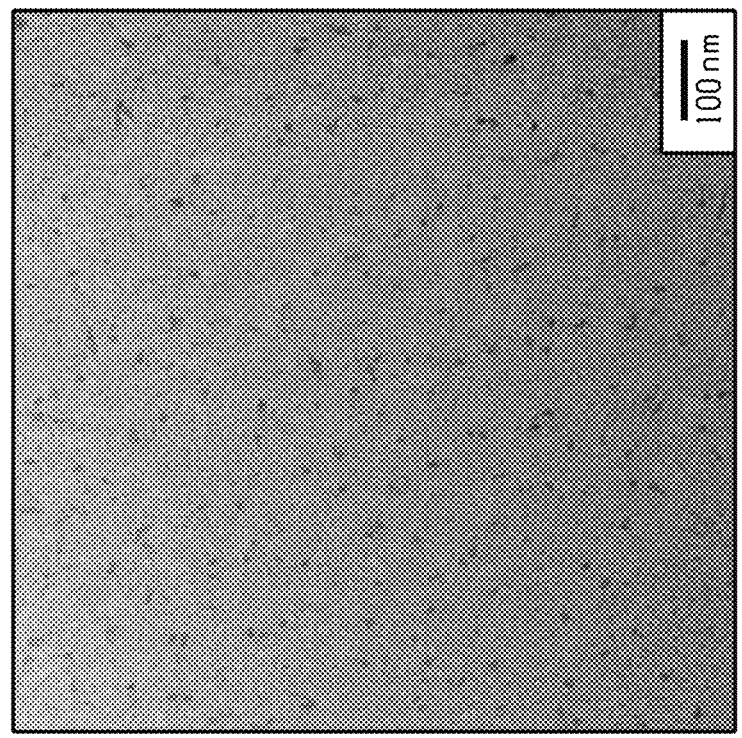
FIG. 6 is a transmission electron micrograph (TEM) of polymer nanoparticles. The scale bar is 100 nanometers (nm).

Polymer nanoparticles were prepared from polymers 7 and 9. In general, the polymer (290 milligrams) was added to water (1 milliliter) to spontaneously form the polymer nanoparticles. The polymer nanoparticles were imaged using transmission election microscopy (TEM), which revealed an average size of 13 nanometers, as shown in FIG. 6. Dynamic light scattering was also used to confirm the size of the polymer nanoparticles, as shown in FIG. 7.

Figure 8:
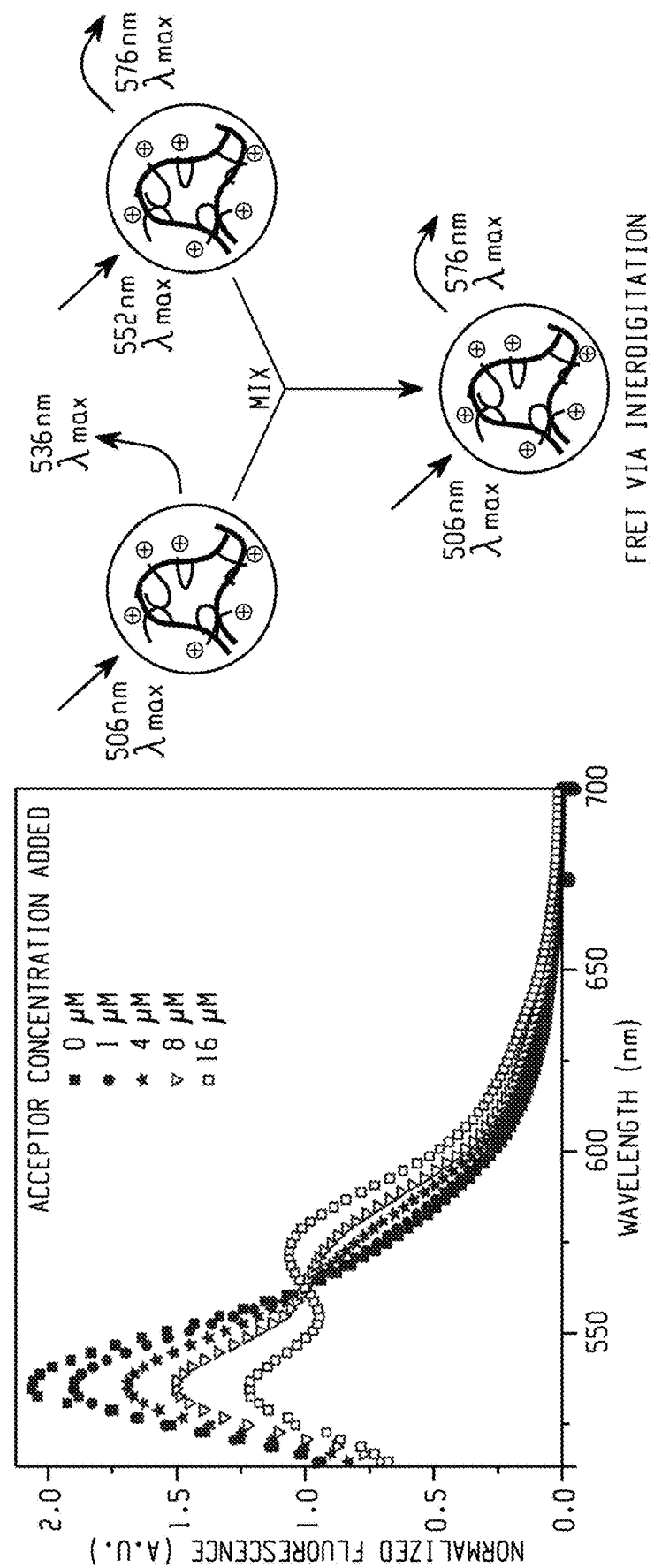
FIG. 8 is a schematic illustration of the Förster Resonance Energy Transfer (FRET) results obtained for the polymer nanoparticles, as well as a schematic illustration of the FRET process.

To confirm the structure of the nanoparticles, FRET experiments were performed on the poly(oxanorbomeneimide)undecyl trimethylammonium analog (Polymer 7 trimethylammonium analog (P7-TMA). By functionalizing P7-TMA polymers with dyes that exhibit FRET (a dye which acts as an electron transfer agent (donor) and an electron acceptor agent (acceptor)) and upon mixing these two in aqueous environments, FRET was observed by the energy transfer from the donor to the acceptor. The FRET results, as well as a schematic illustration of the FRET process, are shown in FIG. 8.

Biological Evaluation

Determination of Antimicrobial Activities of Cationic Polymers: Bacteria were cultured in LB medium at 37° C. and 275 rpm until stationary phase. The cultures were then harvested by centrifugation and washed with 0.85% sodium chloride solution three times. Concentrations of resuspended bacterial solution were determined by optical density measured at 600 nanometers. M9 medium was used to make dilutions of bacterial solution to a concentration of $1 \times 10^6$ cfu/mL. A volume of 50 microliters of these solutions was added into a 96-well plate and mixed with 50 microliters of polymer solutions in M9 medium, giving a final bacterial concentration of $5 \times 10^5$ cfu/mL. Polymer concentration was varied according to a standard protocol, ranging from 1024 to 4 nanomolar (nM). A growth control group without polymers and a sterile control group with only growth medium were carried out at the same time. Incubation of the polymers with bacteria was performed for 16 hours. Cultures were performed in triplicates, and at least two independent experiments were repeated on different days. The minimal inhibitor concentration (MIC) is defined as the lowest concentration of polymer that inhibits visible growth as observed with the unaided eye.

Determination of Hemolysis of Cationic Polymers: Citrate-stabilized human whole blood (pooled, mixed gender) was purchased from Bioreclamation LLC, NY and processed as soon as received. 10 milliliters of phosphate buffered saline (PBS) was added to the blood and centrifuged at 5000 rpm for 5 minutes. The supernatant was carefully discarded and the red blood cells (RBCs) were dispersed in 10 milliliters of PBS. This step was repeated at least five times. The purified RBCs were diluted in 10 milliliters of PBS and kept on ice during the sample preparation. 0.1 milliliter of RBC solution was added to 0.4 milliliters of polymer solution in PBS in a 1.5 milliliter centrifuge tube (Fisher) and mixed gently by pipetting. RBCs incubated with PBS and water was used as negative and positive controls, respectively. All polymer samples as well as controls were prepared in triplicate. The mixture was incubated at 37° C. for 30 minutes while shaking at 150 rpm. After incubation period, the solution was centrifuged at 4000 rpm for 5 minutes and 100 microliters of supernatant was transferred to a 96-well plate. The absorbance value of the supernatant was measured at 570 nm using a microplate reader (SpectraMax M2, Molecular devices) with absorbance at 655 nm as a reference. The percent hemolysis was calculated using the following formula:

$$\% \text{ Hemolysis} = \frac{(\text{Sample Absorbance} - \text{Negative Control Absorbance})}{(\text{Positive Control Absorbance} - \text{Negative Control Absorbance})} * 100$$

Propidium Iodide Staining Assay: *E. coli* CD-2, *P. Aeruginosa* ATCC19660 and MRSA CD-489 ($1 \times 10^8$ cfu/mL) were incubated with 1 µM Polymer 7 in M9 media at 37° C. and 275 rpm for 3 hours. The bacteria solutions were then mixed with PI (2 µM) and incubated for 30 minutes in the dark. Five microliters of each sample was placed on a glass slide with a glass coverslip and observed with a confocal laser scanning microscope, Zeiss 510 (Carl Zeiss, Jena, Germany) using a 543 nm excitation wavelength.

Resistance Development: *E. coli* CD-2 was inoculated in M9 medium with 85 nM (⅔ of 128 nM, MIC) of Polymer 7 at 37° C. and 275 rpm for 16 hours. The culture was then harvested and tested for MIC as describe above. *E. coli* CD-2 was cultured without polymer as well every time as a control for comparison of MICs.

Biofilm Formation and treatment: Bacteria were inoculated in lysogeny broth (LB) medium at 37° C. until stationary phase. The cultures were then harvested by centrifugation and washed with 0.85% sodium chloride solution three times. Concentrations of resuspended bacterial solution were determined by optical density measured at 600 nanometers. Seeding solutions were then made in M9 medium to reach an OD600 of 0.1. A 100 microliter amount of the seeding solutions was added to each well of the 96 well microplate. The plates were covered and incubated at room temperature under static conditions for 1 day. The stock solution of polymers was then diluted to the desired level and incubated with the biofilms for 3 hours at 37° C. Biofilms were washed with phosphate buffered saline (PBS) three times and viability was determined using an Alamar Blue assay. Minimal M9 medium without bacteria was used as a negative control.

Table 1 shows a summary of various polymers prepared according to the above procedures, and the results of the biological evaluation of the corresponding polymer nanoparticles.

activity of the particles. Particles from the Example 5 polymer suppressed bacterial proliferation at concentrations ranging from 64 to 128 nanomolar. These polymers showed similar antimicrobial activity against 5 clinical isolates of *E. coli* with different susceptibility to clinical antibiotics (resistant to 1-17 drugs), indicating their ability to evade common mechanisms of bacterial resistance. Additionally, engineered polymers were effective against clinical isolates of Gram-negative *P. aeruginosa* and *E. cloacae* complex. Similarly, Gram-positive strains of *S. aureus* were susceptible to polymer particles from Example 5 including the highly virulent strain of methicillin-resistant *S. aureus* (MRSA). Table 2, below, shows the minimum inhibitory concentrations and therapeutic indices of the polymer particles against various uropathogenic clinical isolate bacterial strains. Therapeutic indices are calculated with respect to red blood cells.

TABLE 2

| Strain | Species | MIC (nM) | TI ($HC_{50}$/MIC) |
|---|---|---|---|
| CD-23 | *P. aeruginosa* | 64 | 2300 |
| CD-1006 | *P. aeruginosa* | 128 | 1200 |
| CD-489 | *S. aureus* (MRSA) | 64 | 2300 |
| CD-2 | *E. coli* | 128 | 1200 |
| CD-3 | *E. coli* | 64 | 2300 |
| CD-19 | *E. coli* | 64 | 2300 |
| CD-549 | *E. coli* | 128 | 1200 |
| CD-496 | *E. coli* | 128 | 1200 |
| CD-866 | *E. cloacae* | 128 | 1200 |
| CD-1412 | *E. cloacae* | 128 | 1200 |
| CD-1545 | *E. cloacae* | 128 | 1200 |

The polymer nanoparticles were also observed to be particularly effective in disrupting the bacterial cell membrane, which, without wishing to be bound by theory, is believed to be due to the highly cationic and hydrophobic nature of the nanoparticles. This was demonstrated using a propidium iodide (PI) staining assay. PI only stains cells having compromised cell membranes, allowing them to bind with nucleic acids and generate red fluorescence. Pathogenic *E. coli* (CD-2), *S. aureus* (CD-489), and non-pathogenic *P. aeruginosa*(ATCC 19660) were treated with 1 micromolar

TABLE 1

| Ex. | Polymer | R Group | Molecular Weight (kg/mol) | MIC (µg/ml) *P. aeruginose* | $HC_{50}$ (ug/ml) | Selectivity ($HC_{50}$/MIC) *P. aeruginose* |
|---|---|---|---|---|---|---|
| 1 | 9 | Methyl | 20 | 2.5 | 402 | 160 |
| 2 | 9 | Ethyl | 20 | 2.7 | 417 | 160 |
| 3 | 9 | Butyl | 22 | 1.4 | 446 | 330 |
| 4 | 9 | Decyl | 22 | 2.0 | 25 | 10 |
| 5 | 7 | Methyl | 29 | 0.9 | 4700 | 5000 |
| 6 | 7 | Ethyl | 30 | 1.9 | 9700 | 5000 |
| 7 | 7 | Butyl | 32 | 4.6 | ND | ND |
| 8 | 7 | Hexyl | 34 | 2.4 | ND | ND |
| 9 | 7 | Benzyl | 34 | 4.8 | ND | ND |

"ND" means not determined.

The polymeric nanoparticles described above possess low minimal inhibitor concentrations (MICs) in the range of 0.1 to 5.0 ug/mL, specifically 0.5 to 5.0 ug/mL, towards pathogenic planktonic bacteria while maintaining remarkable hemolytic activities (therapeutic index: hemolysis (50%)/MIC~5,000 for Example 5).

Polymer particles of the polymer of Example 5 were further tested against multiple uropathogenic clinical isolates, listed in Table 2, to demonstrate the broad spectrum solution of nanoparticles of Example 5 for 3 hours at 37° C. and subsequently stained with PI before imaging. Confocal microscopy was used to show that the polymer nanoparticle mechanism of action leads to bacterial membrane disruption in all three species, regardless of membrane composition or pathogenicity.

In addition, the present inventors have demonstrated effective killing of pathogenic biofilms, not yet observed from other polymer researchers. The biofilm eradication data for the polymer of Example 5 in Table 1 (i.e., oxanorbornene polymer backbone with a $C_{11}$ spacer and a trimethyl ammonium head group) is shown in FIG. 9-12. The Example 5 polymer was incubated with the biofilm at varying concentrations, and bacterial viability was determined for each, as described above. FIG. 9-12 generally demonstrate that polymer nanoparticle concentrations which cause an increase in viability is likely due to the phenomenon called "hormesis", a biological response to low exposures to toxins and other stressors. As the concentration of polymer nanoparticles increases (e.g., to greater than 500 nanomolar), viability was observed to decrease indicating the killing of the bacteria within the biofilms. In general, the present inventors have observed that complete eradication of the biofilms can occur at concentrations of at least 2 µM.

Figure 9:
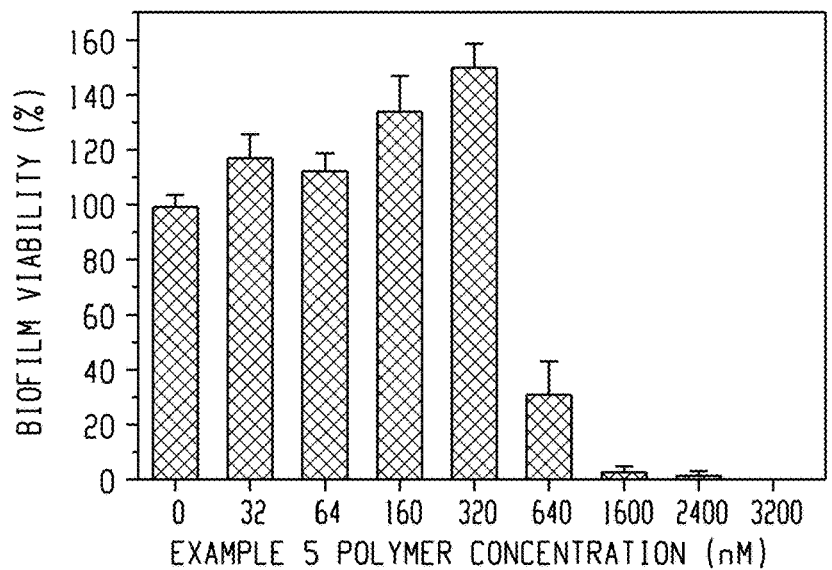
FIG. 9 shows the viability of a *P. aeruginosa* ATC-19660 biofilm when contacted with varying concentrations of polymer nanoparticles.
Figure 10:
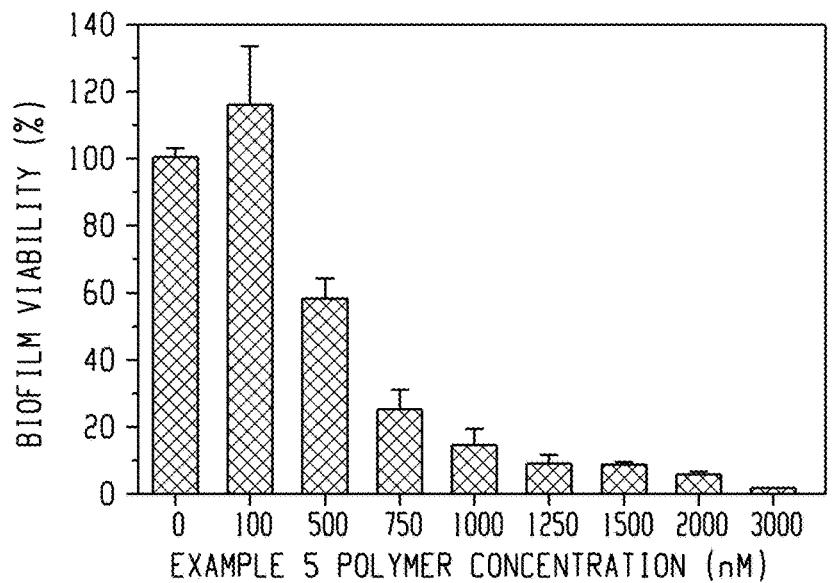
FIG. 10 shows the viability of a *S. aureus* (MRSA) biofilm with varying concentrations of polymer nanoparticles.
Figure 11:
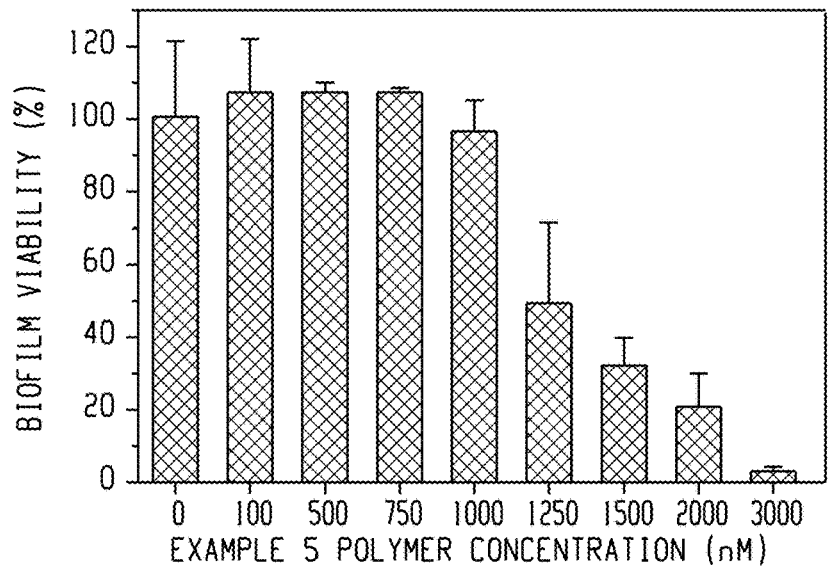
FIG. 11 shows the viability of a *P. aeruginosa* CD-1006 biofilm with varying concentrations of polymer nanoparticles.
Figure 12:
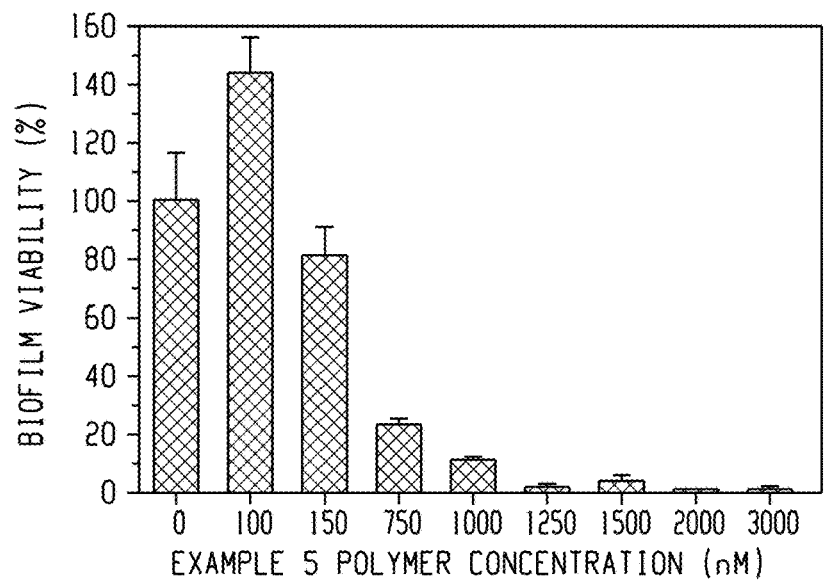
FIG. 12 shows the viability of a *E. cloacae* CD-1412 biofilm with varying concentrations of polymer nanoparticles.

FIG. 9 shows that the Example 5 polymer could effectively eradicate the P. aeruginosa ATC-19660 biofilm at a concentration of greater than 640 nM. FIG. 10 shows that the Example 5 polymer could effectively eradicate the S. aureus (MRSA) biofilm at a concentration of greater than 2 µM. FIG. 11 shows that the Example 5 polymer could effectively eradicate the P. aeruginosa CD-1006 biofilm at a concentration of greater than 2 µM. FIG. 12 shows that the Example 5 polymer could effectively eradicate the E. cloacae CD-1412 biofilm at a concentration of greater than 1 µM.

Figure 13:
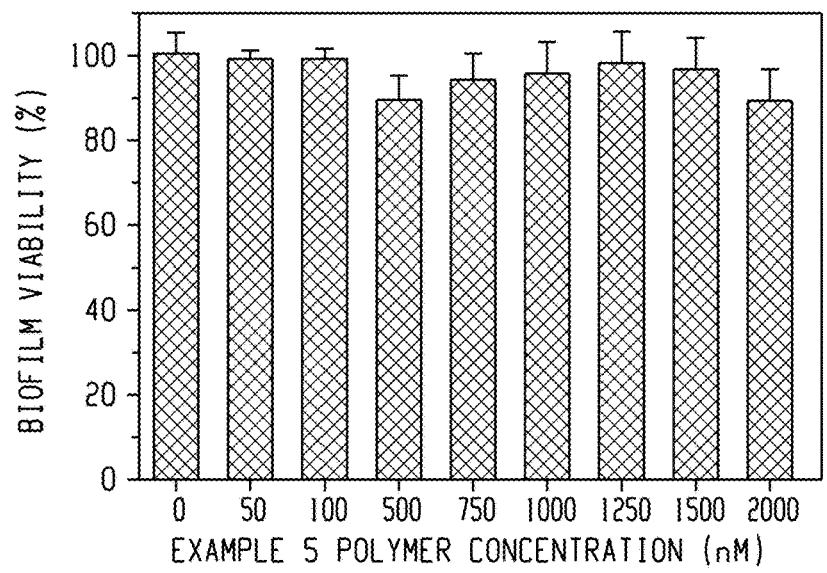
FIG. 13 shows the viability of macrophages with varying concentrations of polymer nanoparticles.
Figure 14:
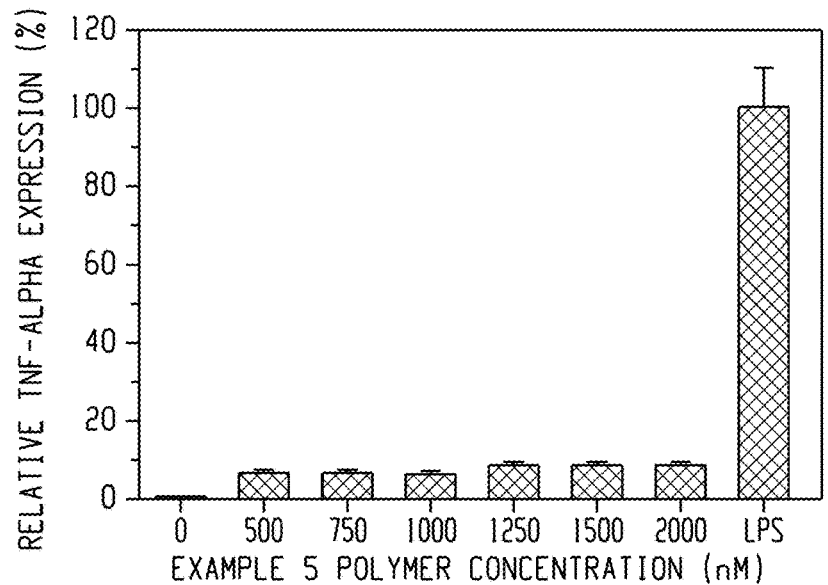
FIG. 14 shows relative TNF-α expression with varying concentrations of polymer nanoparticles.

As shown in FIG. 13, the polymer of Example 5 was also demonstrated to be non-toxic to macrophages, with greater than 80% viability observed from polymer concentrations of 20 nM to 2 µM. Furthermore, as shown in FIG. 14, the polymer nanoparticles were not observed to cause macrophage cells to release inflammatory cytokine TNF-alpha, suggesting the polymer nanoparticles are immunocompatible. LPS is used as a positive control, which induces cytokine expression in macrophages.

Figure 15:
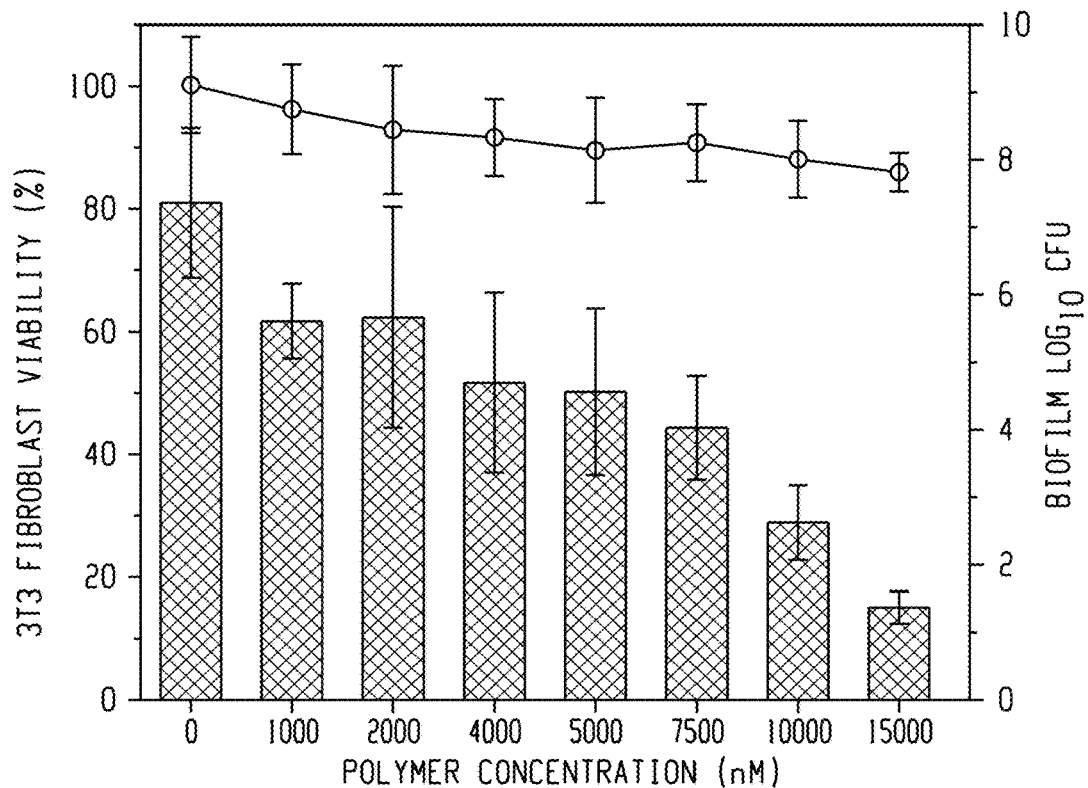
FIG. 15 shows toxicity of polymer nanoparticles to *P. aeruginosa* (ATCC-19660) biofilms that are grown in the presence of 3T3 fibroblast cells.

The ability to eradicate biofilms on human tissue or organs is also of significant importance. An in vitro co-culture model of mammalian fibroblast cells with biofilms grown over them was used. First, compatibility of the polymer particles was tested using the Example 5 polymer with NIH 3T3 fibroblast cells at similar concentrations used to eradicate the pre-formed biofilms. No significant toxicity was observed. Next, P. aeruginosa bacteria was seeded on a confluent monolayer of NIH 3T3 fibroblast cells overnight to generate biofilms prior to treatment. The co-cultures were treated with the Example 5 polymer nanoparticles for 3 hours, washed, and the viabilities of both bacteria and fibroblasts were determined. As shown in FIG. 15, a 4-6-fold log reduction in bacterial colonies was observed at concentrations ranging from 7.5 to 15 micromolar, while fibroblast viability was maintained.

Figure 16:
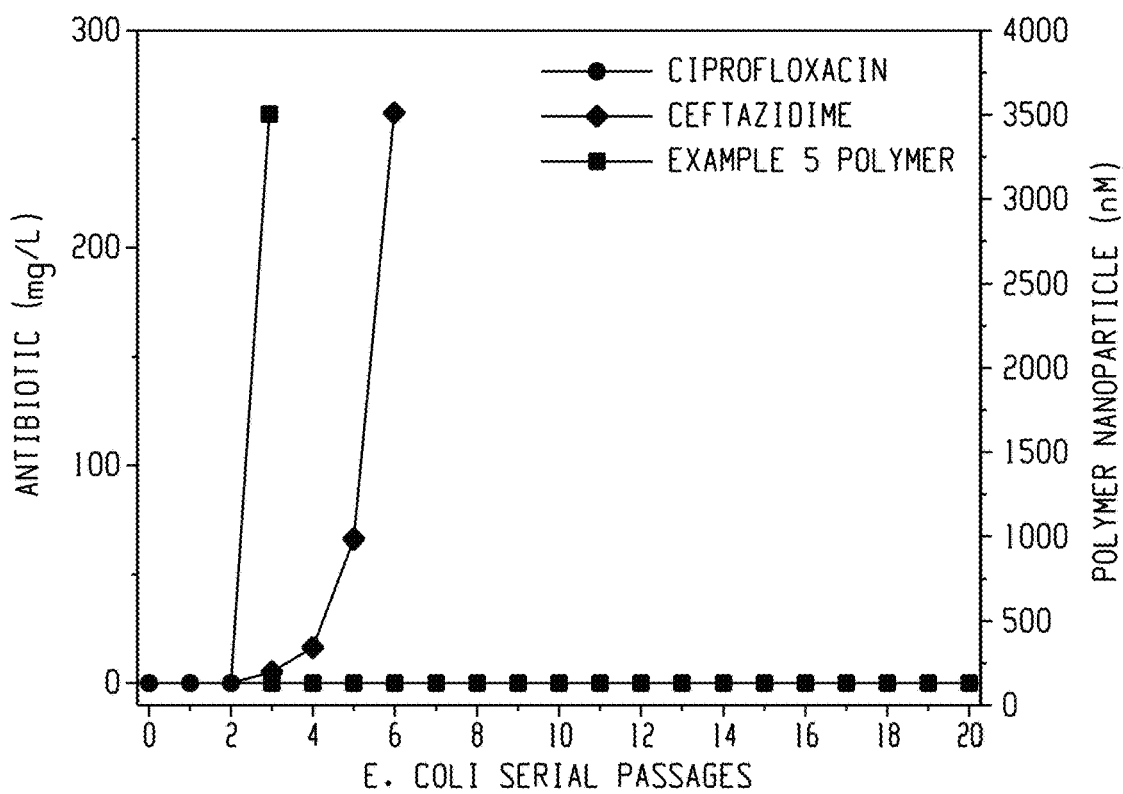
FIG. 16 shows resistance development during serial passaging in the presence of sub-MIC levels of antimicrobials.

Bacteria are capable of acquiring resistance quickly towards antibiotics and other antimicrobials, minimizing their therapeutic prospects in clinical settings. The present inventors subjected uropathogenic E. coli (CD-2) to multiple serial passages of sub-MIC (66% of MIC) concentrations of Example 5 polymer nanoparticles to investigate if resistance towards the present polymer nanoparticles occurs. The resulting bacterial population was defined as the first generation, harvested, and its MIC was evaluated. Subsequently, a second generation was produced by exposing first generation with 66% MIC dosage of polymers. As shown in FIG. 16, it was observed that even at the $20^{th}$ serial passage (about 1300 bacterial generations) of CD-2, E. coli was still susceptible to 128 nanomolar of Example 5 polymer nanoparticles, as compared to the zero generation. Similar experiments were conducted on ciprofloxacin (quinolone) and ceftazidime (0-lactam), clinically relevant antibiotics. Respectively, there was a 33,000 and 4,200-fold increase in the MICs of antibiotics against CD-2 E. coli. This significant result indicates the killing mechanism of the present polymer nanoparticles significantly undermines the onset of resistance development in bacteria. Notably, the polymeric nanoparticles remain un-resistant towards bacteria longer than previously reported polymer-based nanomaterials (~600 generations—A. baumannii FADDI-AB156) and comparable to a recently discovered and novel antibiotic, teixobactin (~1,300 generations—S. aureus ATCC 29213).

Polymer Nanoparticles for Theranostics

Figure 17:
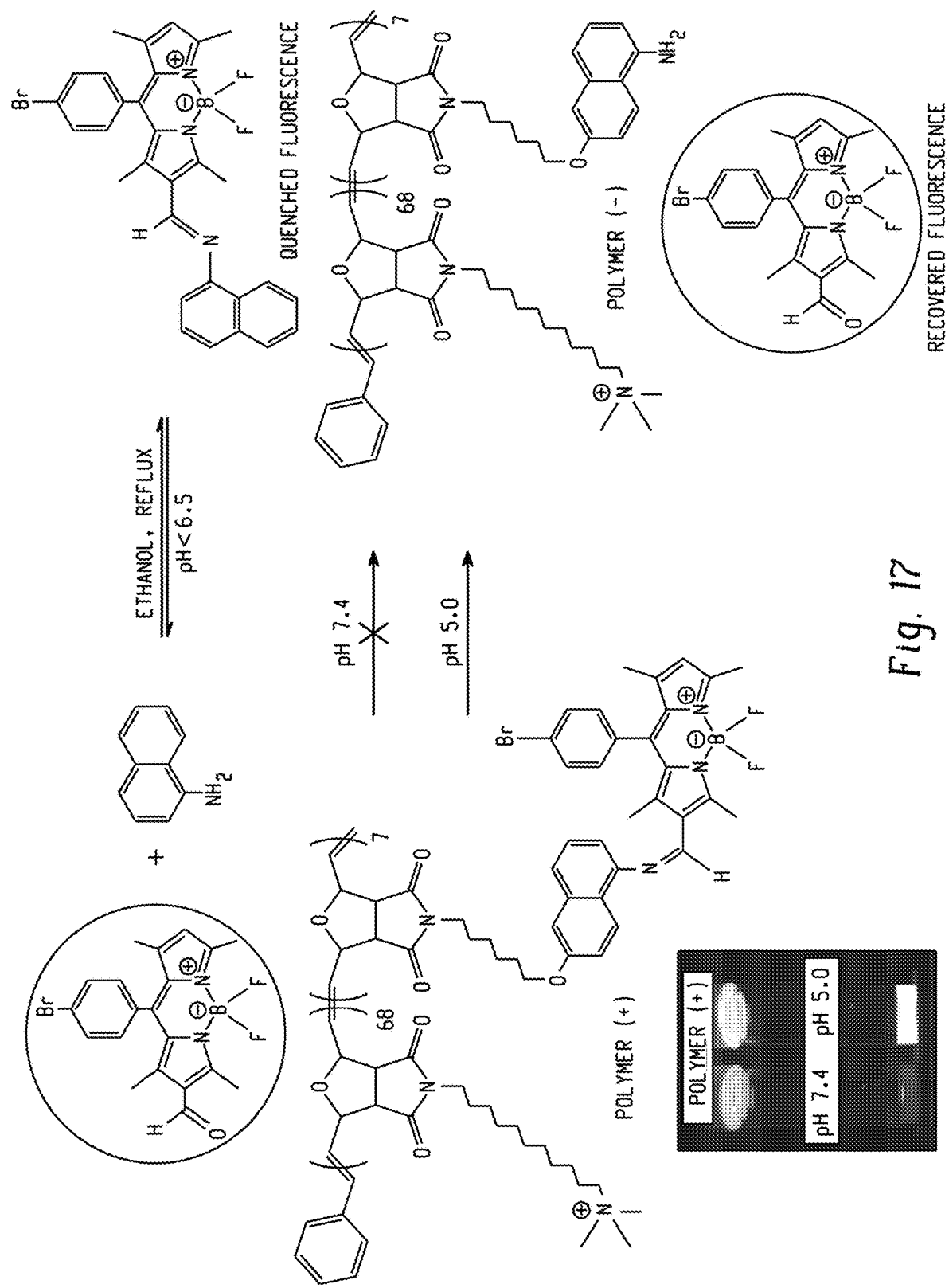
FIG. 17 illustrates the mechanism of fluorescence for pH-sensitive fluorophore tagged polymers, showing that the quenched dye will recover its fluorescence in acidic environments.

The present inventors have further developed a method for preparing biofilm theranostic agents from the above described polymer nanoparticles. "Theranostic" as used herein means the polymer nanoparticles are capable of serving both as a diagnostic tool, as well as a therapeutic agent. The present inventors have taken advantage of the highly acidic environment of a bacterial biofilm, and conjugated a fluorescent dye via a pH sensitive linkage to the polymer used to prepare the polymer nanoparticles. In the conjugated form, the fluorescence of the dye is quenched. Upon incubating the particles with the biofilms, acid-mediated hydrolysis of the dye linker restores fluorescence. This aspect of the present disclosure provides a new tool for imaging a biofilm. A schematic representation of this aspect is illustrated in FIG. 17.

Fluorescently tagged polymers were prepared according to the same general procedure described above, except that a comonomer including the fluorescent dye (e.g., BODIPY) was included. The resulting polymer included the trimethylammonium-containing monomer having an eleven carbon spacer and the dye-containing comomoner in a ratio of 68:7. As described above, the polymer was self-assembled into polymer nanoparticles in aqueous solution, where the fluorescence of the dye was observed to be quenched. Upon exposure to an acidic environment (e.g., pH 5.0), the dye was released from the polymer nanoparticles and the free BODIPY dye fluorescence was observed.

Biofilms of E. coli DH5α were used to test the ability of the fluorescently tagged polymer nanoparticles to penetrate and image the biofilms. $10^8$ bacterial cells/milliliter (DS Red exp. E. coli) were seeded (2 milliliters in M9 media with 1 mM IPTG) in a confocal dish and were allowed to grow, old media was replaced every 24 hours. After 3 days media was replaced by 1 µM of the polymeric nanoparticles were added to biofilms and were incubated for 1 hour. After 1 hour, biofilms were washed with PBS three times. Confocal microscopy images were obtained on a Zeiss LSM 510 Meta microscope by using a 63× objective. The settings of the confocal microscope were as follows: green channel: $\lambda_{ex}$=488 nm and $\lambda_{em}$=BP 505-530 nm; red channel: $\lambda_{ex}$=543 nm and $\lambda_{em}$=LP 650 nm. Emission filters: BP=band pass, LP=high pass.

Figure 18A:
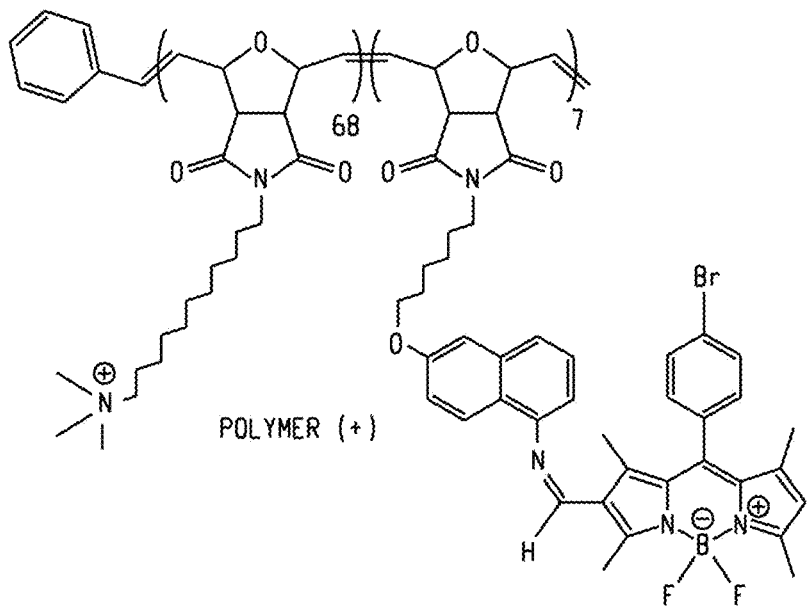
FIG. 18A shows the chemical structures of a BODIPY dye, a polymer without dye ("Polymer(−)"), and a polymer with dye ("Polymer(+)").
Figure 18A:
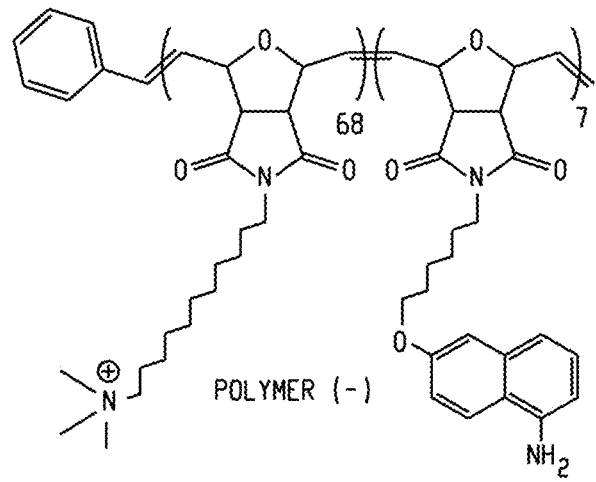
Figure 18A:
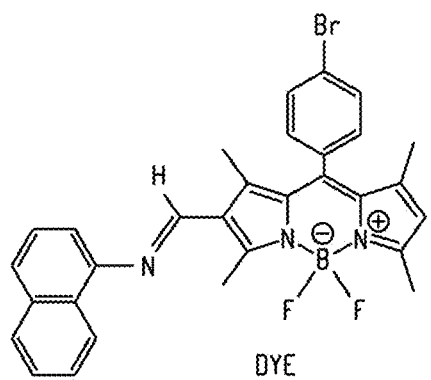
Figure 18B:
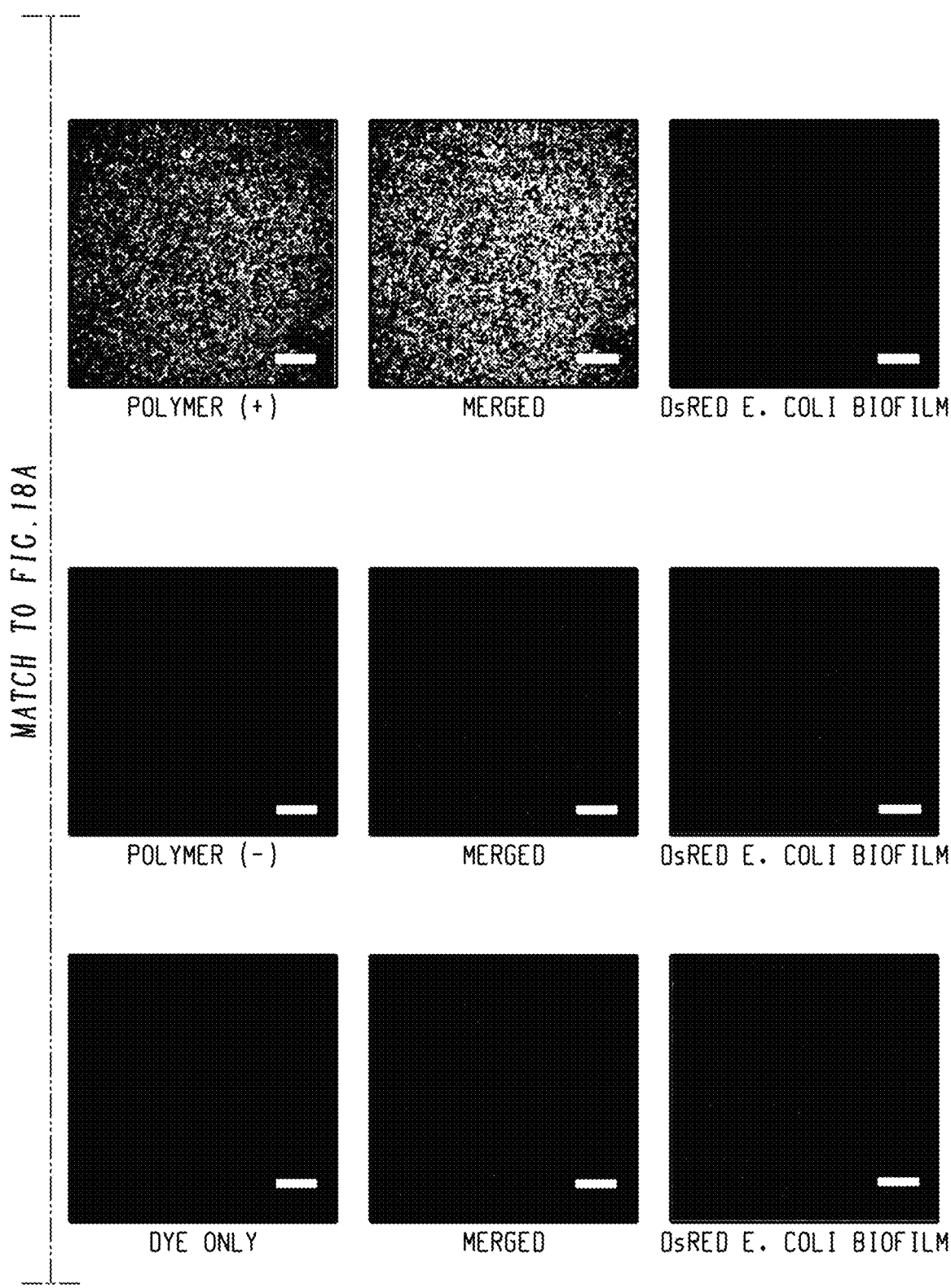
FIG. 18B shows confocal microscopy images of the BODIPY dye, the polymer without dye ("Polymer(−)"), and the polymer with dye ("Polymer(+)") of FIG. 18A after incubation with a biofilm, indicating fluorescence recovery of the fluorescent dye as the polymer nanoparticles penetrate the biofilm. The negative control of polymer without dye (middle row) shows no green fluorescence. Scale bars are 30 micrometers.
Figure 19:
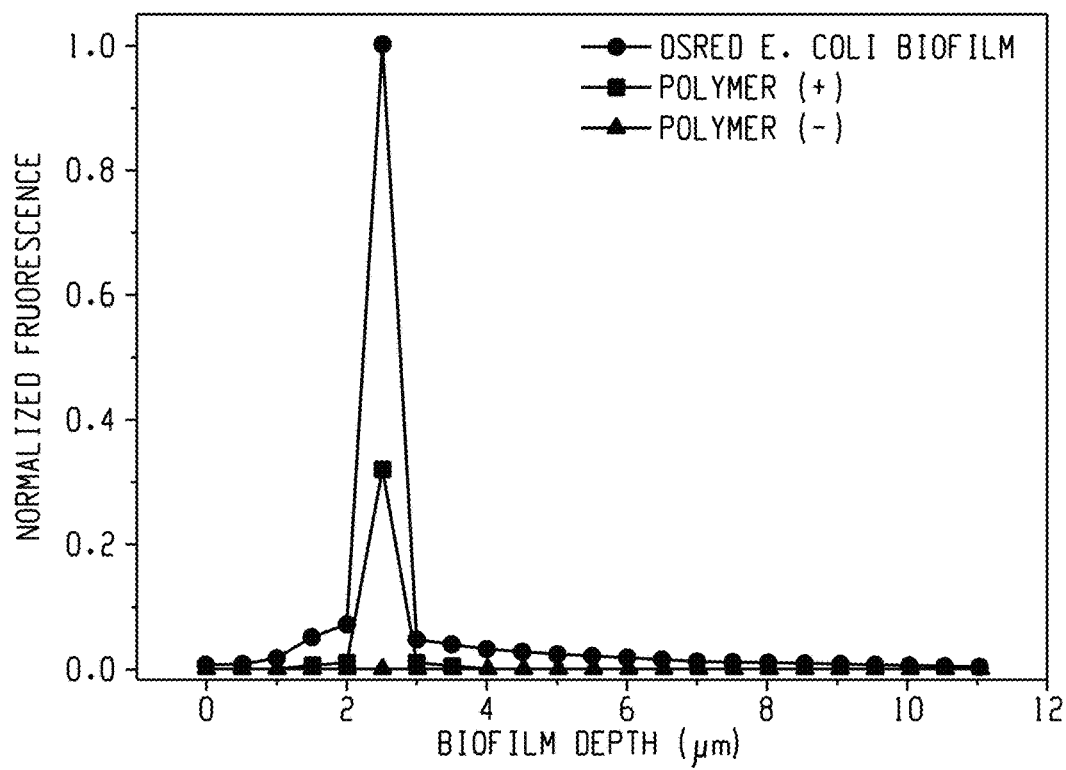
FIG. 19 is a plot of normalized fluorescence intensities with respect to biofilm depth.

Confocal images are shown in FIG. 18B. FIG. 18B, top row, shows the fluorescence recovery of the dye as the polymer nanoparticles penetrate the biofilm. The negative control (polymer without dye, middle row) shows no green fluorescence. A negative control of dye only shows no green fluorescence due to lack of the presence of the dye after washing (i.e., lack of the ability of the dye alone to penetrate the biofilm). FIG. 19 shows the normalized fluorescence intensities with respect to biofilm depth. From FIG. 19, it can be seen that polymer nanoparticles including BODIPY dyes ("Polymer(+)") generate fluorescence while dye-free polymer nanoparticles ("Polymer(-)") show no fluorescence.

Co-delivery of Polymer Nanoparticles and Antibiotics for Therapeutic Synergy

As will be demonstrated by the following examples, the present inventors have further discovered that co-incubation of polymer nanoparticles and an antibiotic, colistin, with planktonic bacteria or biofilms produces a synergistic therapeutic response. Importantly, enhanced colistin uptake into biofilms with nanoparticles were present was observed, determined by an increase in colistin fluorescence within the biofilm (colistin was labeled with a fluorophore for imaging purposes). Without wishing to be bound by theory, it is believed that the enhanced uptake of the antibiotic into the biofilm can be attributed to the ability of the polymer nanoparticles to both penetrate the biofilm matrix and disrupt bacterial membranes, providing colistin with an avenue to enter biofilms and bind the membrane target.

To assess possible synergy between antibiotics and polymeric nanoparticles, two-dimensional checkerboard titrations were performed using a micro-dilution method. In 96-well plates, 2-fold dilutions of antibiotics against a range of 2-fold dilutions of nanoparticles were used to determine the MIC of the combinations. The concentrations of nanoparticles were varied from their MIC to $\frac{1}{32}*h$ of their MIC. Similarly the concentrations of antibiotics were varied from their MIC to $\frac{1}{32}*h$ of their MIC. The checkerboard titrations were performed in a set of three independent experiments, repeated on different days.

Antibiotic-nanoparticle interaction was determined by calculating the fractional inhibitory concentration of antibiotics ($FIC_{Ab}$) and NPs ($FIC_{NP}$) according to the following equations:

$$FIC_{Ab} = (MIC\ of\ antibiotic\ and\ NP\ combination) \div (MIC\ of\ antibiotic\ alone)$$

$$FIC_{NP} = (MIC\ of\ antibiotic\ and\ NP\ combination) \div (MIC\ of\ NP\ alone)$$

$$FICI_{combination} = FIC_{Ab} + FIC_{NP}$$

Figure 20:
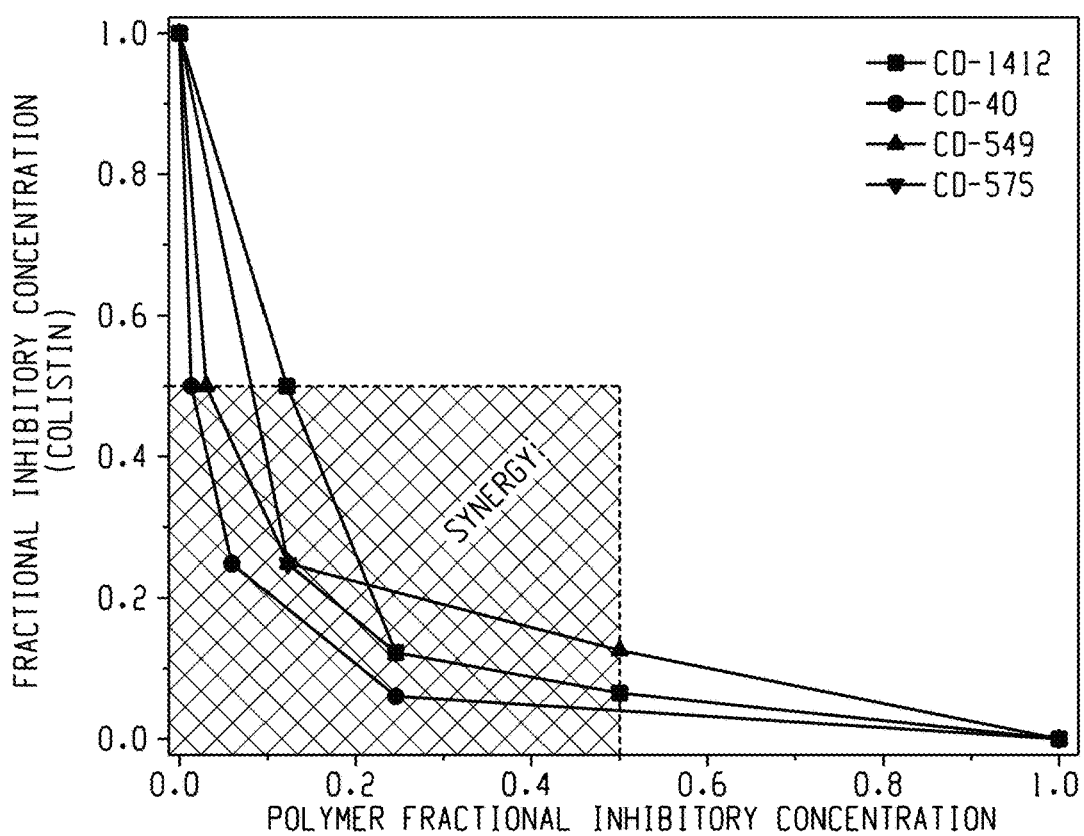
FIG. 20 is a plot showing the region in which therapeutic synergy can be obtained for the polymer nanoparticles and the antibiotic colistin.

$FIC_{Ab}$ was plotted against $FIC_{NP}$. A concave curve indicates synergy, whereas a convex curve indicates antagonism. Synergy was defined as FICI values ≤0.5, antagonism by FICI values >4.0, and additive interaction by FICI values between >0.5 and 4.0. The experiments were conducted across four different planktonic bacteria strains (*E. clocae* complex "CD-1412"; *Pseudomonas aeruginosa* "CD-40"; *E. coli* "CD-549"; and *Acinetobacter* species "CD-575"). A plot of the results is shown in FIG. 20. As shown in FIG. 20, the polymer nanoparticles are therapeutically synergistic with membrane binding antibiotics such as colistin. In the presence of polymer nanoparticles, colistin's uptake in biofilms is enhanced nearly 3.5 times. These results suggest that bacteria can become more susceptible to certain antibiotics when polymer nanoparticles are co-added.

The uptake of colistin into the bacterial biofilms was also analyzed. $10^8$ bacterial cells/ml (DS Red exp *E. coli*) were seeded (2 ml in M9 media, 1 mM IPTG) in a confocal dish and were allowed to grow, and old media was replaced every 24 hours. Testing solutions of coumarin-tagged polymer (1-1.5 µM), rhodamine conjugated colistin (10-20 mg/L) and a combination of both were prepared. After 3 days media was replaced by the prepared testing solutions and biofilms were incubated for 1 hour, biofilm samples incubated with only M9 media were used as control. After 1 hour, biofilms were washed with PBS three times and confocal microscopy images were obtained on a Zeiss LSM 510 Meta microscope by using a 63× objective. The results show that when polymer nanoparticles are added along with colistin to biofilms, an enhancement in colistin uptake occurs (observed as green fluorescence arising from a rhodamine G label that was conjugated to the colistin for imaging purposed), determined using confocal microscopy.

Figure 21:
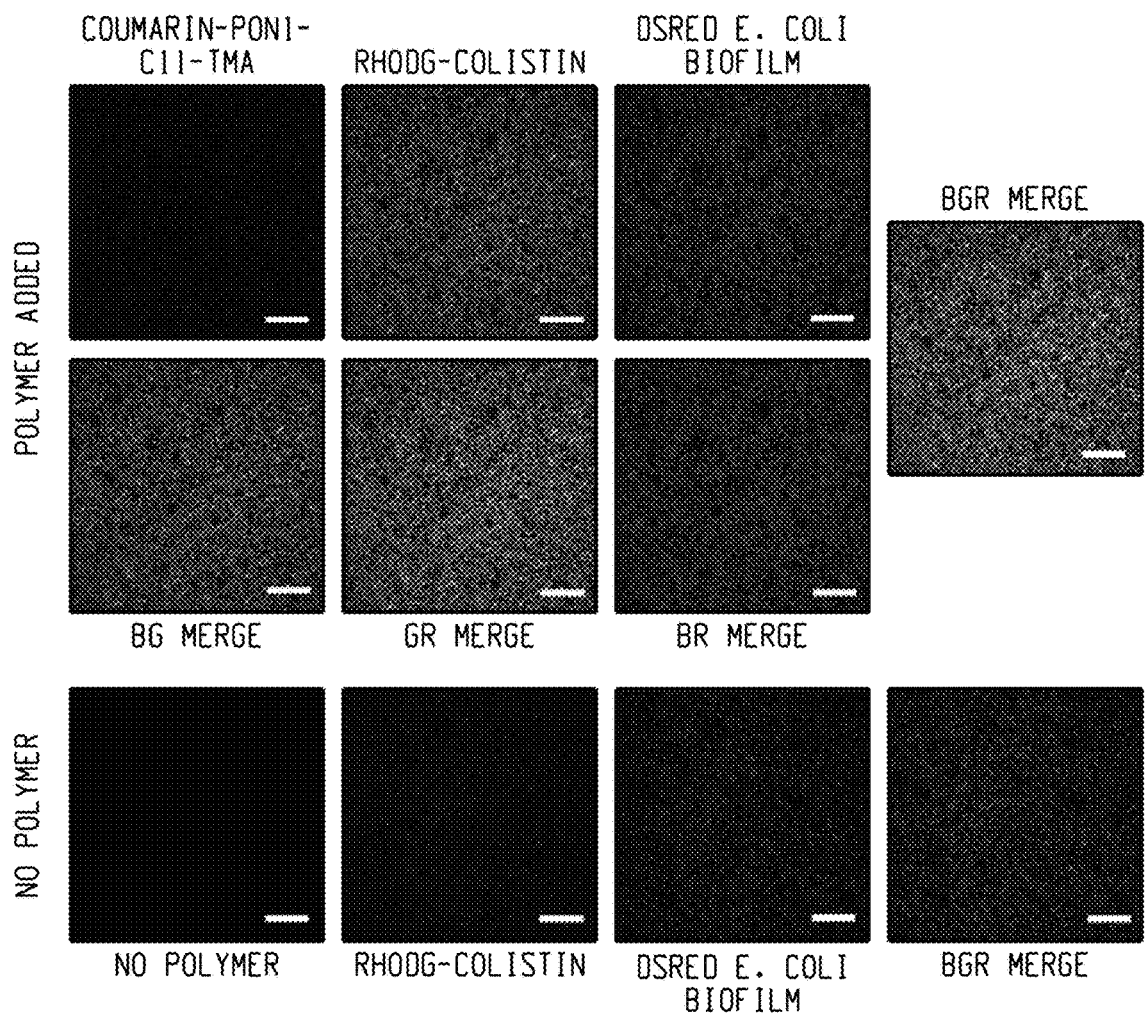
FIG. 21 shows confocal microscopy images showing that when polymer nanoparticles are incubated with colistin, enhanced colistin uptake is observed. Scale bars are 30 micrometers.
Figure 22:
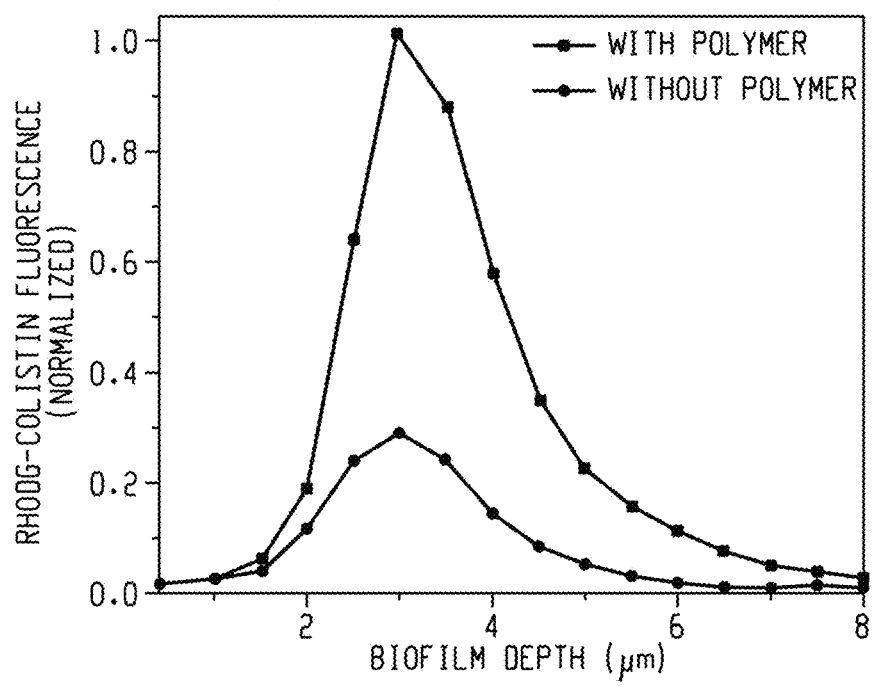
FIG. 22 shows quantitative analysis of colistin uptake with and without polymer based on normalized rhodamine-G-labelled colistin fluorescence.

Co-localization was observed between bacteria (red fluorescence), colistin (green fluorescence), and polymer nanoparticles (blue fluorescence). The confocal images of coumarin labeled polymer, rhodamine labeled colistin, and red fluorescent bacteria as well as their overlays, and the control when no polymer is present are provided in FIG. 21 (scale bars are 30 µm, biofilms are *E. coli* DH5α). FIG. 22 shows a plot of the quantitative analysis of the images shown in FIG. 21. Using observed fluorescence from the rhodamine-labeled colistin, it can be seen that, in the presence of the polymer, colistin uptake in the biofilm is enhanced, compared to when no polymer is added. Integrating and comparing the area under each of these curves shows that colistin uptake is enhanced by about 3.4 times when the polymer is present.

The polymers, polymer nanoparticles, and methods of the present disclosure include at least the following embodiments.

Embodiment 1: A polymer nanoparticle comprising, a polymer comprising repeating units of formula (I), wherein X is independently at each occurrence —O—, —S—, —CH$_2$—, —(CR$^4$R$^5$)—, or

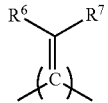

wherein R$^4$ and R$^5$ are independently at each occurrence a C$_{1-6}$ alkyl group and R$^6$ and R$^7$ are independently at each occurrence hydrogen or a C$_{1-6}$ alkyl group; L$^1$ is independently at each occurrence a divalent group that is (—CH$_2$—)$_z$, wherein z is an integer from 3 to 18; and R$^1$ is independently at each occurrence an ammonium group, a phosphonium group, a zwitterionic group, a carboxylate group, a sulfonate group, an alkylene oxide group, or a combination thereof.

Embodiment 2: The polymer nanoparticle of embodiment 1, wherein the nanoparticle has a diameter of 1 to 100 nanometers.

Embodiment 3: The polymer nanoparticle of embodiment 1 or 2, wherein X is —O—.

Embodiment 4: The polymer nanoparticle of embodiment 1 or 2, wherein X is —CH$_2$—.

Embodiment 5: The polymer nanoparticle of any one of embodiments 1 to 4, wherein z is an integer from 6 to 12.

Embodiment 6: The polymer nanoparticle of any one of embodiments 1 to 5, wherein R$^1$ is an ammonium-containing group of formula (II), wherein R$^2$ is a C$_{1-12}$ alkyl group or a C$_{7-20}$ alkylaryl group; and Y is bromide, chloride, fluoride, iodide, hydroxide, phosphate, sulfonate, carbonate, acetate, hexafluorophosphate, tetrafluoroborate, mesylate, trifluoroacetate, p-toluenesulfonate, or a combination thereof.

Embodiment 7: The polymer nanoparticle of any one of embodiments 1 to 6, wherein X is —O—; z is an integer from 6 to 12; and R$^1$ is an ammonium-containing group of formula (II), wherein R$^2$ is a C$_{1-6}$ alkyl group or a benzyl group and Y is bromide, hydroxide, or a combination thereof.

Embodiment 8: The polymer nanoparticle of any one of embodiments 1 to 6, wherein X is —$CH_2$—; z is an integer from 6 to 12; and $R^1$ is an ammonium-containing group of formula (II), wherein $R^2$ is a $C_{1-10}$ alkyl group, and Y is bromide, hydroxide, or a combination thereof.

Embodiment 9: The polymer nanoparticle of any one of embodiments 1 to 8, wherein the polymer further comprises repeating units of formula (VIII), wherein X is independently at each occurrence —O—, —S—, —$CH_2$—, —($CR^4R^5$)—, or

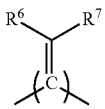

wherein $R^4$ and $R^5$ are independently at each occurrence a $C_{1-6}$ alkyl group and $R^6$ and $R^7$ are independently at each occurrence hydrogen or a $C_{1-6}$ alkyl group; and $L^3$ is independently at each occurrence a $C_{3-20}$ alkyl group.

Embodiment 10: The polymer nanoparticle of any one of embodiments 1 to 9, wherein the polymer further comprises repeating units of formula (IX), wherein X is independently at each occurrence —O—, —S—, —$CH_2$—, —($CR^4R^5$)—, or

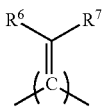

wherein $R^4$ and $R^5$ are independently at each occurrence a $C_{1-6}$ alkyl group and $R^6$ and $R^7$ are independently at each occurrence hydrogen or a $C_{1-6}$ alkyl group; $L^1$ is independently at each occurrence a divalent group that is (—$CH_2$—)$_z$, wherein z is an integer from 3 to 18; Z is independently at each occurrence a divalent group that is (—$CH_2$—)$_z$, wherein z is an integer from 3 to 18; y is 0 or 1; and $R^8$ is a fluorescent group.

Embodiment 11: The polymer nanoparticle of embodiment 10, wherein the repeating units of formula (IX) are present in a molar ratio of repeating units of formula (I):repeating units of formula (IX) of 15:1 to 5:1.

Embodiment 12: The polymer nanoparticle of any one of claims 1 to 11, wherein the polymer has a weight average molecular weight of 5,000 to 100,000 grams per mole.

Embodiment 13: A method of making the polymer nanoparticle of any one of embodiments 1 to 12, the method comprising combining the polymer comprising repeating units of formula (I) and an aqueous solution.

Embodiment 14: A polymer comprising repeating units of formula (I), wherein X is independently at each occurrence —O—, —S—, —$CH_2$—, —($CR^4R^5$)—, or

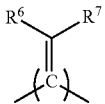

wherein $R^4$ and $R^5$ are independently at each occurrence a $C_{1-6}$ alkyl group and $R^6$ and $R^7$ are independently at each occurrence hydrogen or a $C_{1-6}$ alkyl group; $L^1$ is independently at each occurrence a divalent group that is (—$CH_2$—)$_z$, wherein z is an integer from 3 to 18; and $R^1$ is independently at each occurrence an ammonium group, a phosphonium group, a zwitterionic group, a carboxylate group, a sulfonate group, an alkylene oxide group, or a combination thereof.

Embodiment 15: The polymer of embodiment 14, wherein X is —O—.

Embodiment 16: The polymer of embodiment 14, wherein X is —$CH_2$—.

Embodiment 17: The polymer of any one of embodiments 14 to 16, wherein z is an integer from 6 to 12.

Embodiment 18: The polymer of any one of embodiments 14 to 17, wherein $R^1$ is an ammonium-containing group of formula (II), wherein $R^2$ is a $C_{1-12}$ alkyl group or a $C_{7-20}$ alkylaryl group; and Y is bromide, chloride, fluoride, iodide, hydroxide, phosphate, sulfonate, carbonate, acetate, hexafluorophosphate, tetrafluoroborate, mesylate, trifluoroacetate, p-toluenesulfonate, or a combination thereof.

Embodiment 19: The polymer of any one of embodiments 14 to 18, wherein X is —O—; z is an integer from 6 to 12; and $R^1$ is an ammonium-containing group of formula (II), wherein $R^2$ is a $C_{1-6}$ alkyl group or a benzyl group and Y is bromide, hydroxide, or a combination thereof.

Embodiment 20: The polymer of any one of embodiments 14 to 18, wherein X is —$CH_2$—; z is an integer from 6 to 12; and $R^1$ is an ammonium-containing group of formula (II), wherein $R^2$ is a $C_{1-10}$ alkyl group, and Y is bromide, hydroxide, or a combination thereof.

Embodiment 21: The polymer of any one of embodiments 14 to 20, wherein the polymer has a weight average molecular weight of 5,000 to 100,000 grams per mole.

Embodiment 22: The polymer of any one of embodiments 14 to 21, further comprising repeating units of formula (VIII), wherein X is independently at each occurrence —O—, —S—, —$CH_2$—, —($CR^4R^5$)—, or

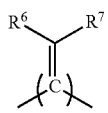

wherein $R^4$ and $R^5$ are independently at each occurrence a $C_{1-6}$ alkyl group and $R^6$ and $R^7$ are independently at each occurrence hydrogen or a $C_{1-6}$ alkyl group; and $L^3$ is independently at each occurrence a $C_{3-20}$ alkyl group.

Embodiment 23: The polymer of any one of embodiments 14 to 22, wherein the polymer further comprises repeating units of formula (IX), wherein X is independently at each occurrence —O—, —S—, —$CH_2$—, —($CR^4R^5$)—, or

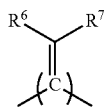

wherein $R^4$ and $R^5$ are independently at each occurrence a $C_{1-6}$ alkyl group and $R^6$ and $R^7$ are independently at each occurrence hydrogen or a $C_{1-6}$ alkyl group; $L^1$ is independently at each occurrence a divalent group that is (—CH$_2$—)$_z$, wherein z is an integer from 3 to 18; Z is a divalent C$_{6-20}$ arylene group, a divalent C$_{1-20}$ alkylene oxide group, a divalent poly(C$_{1-6}$ alkylene oxide) group, or an amino acid containing group; y is 0 or 1; and R$^8$ is a fluorescent group.

Embodiment 24: A method of treating a bacterial biofilm, the method comprising contacting an aqueous composition comprising a plurality of polymer nanoparticles according to any one of claims 1 to 12 or the polymer of any one of claims 14 to 23 with a bacterial biofilm.

Embodiment 25: The method of embodiment 24, wherein the aqueous composition comprises 0.0001 to 1 weight percent of the polymer nanoparticles; and 99 to 99.9999 weight percent of an aqueous solution.

Embodiment 26: The method of any of embodiments 24 to 25, wherein the method further comprises contacting an antibiotic with the bacterial biofilm, preferably wherein the contacting of the antibiotic with the bacterial biofilm occurs simultaneously with the contacting of the aqueous composition and the bacterial biofilm.

Embodiment 27: The method of any one of embodiments 24 to 26, wherein the bacterial biofilm comprises *Escherichia coli*, *Pseudomonas* bacteria, *Staphylococcal* bacteria, *Enterobacter* bacteria, *Streptococcus* bacteria, *Haemophilus influenzae*, *Leptospira interrogans*, *Legionella* bacteria, *Micrococcus* bacteria, *Bacillus* bacteria, *Burkholderia* bacteria, *Amycolatopsis* bacteria, *Mycobacterium* bacteria, *Acinetobacter* bacteria, *Enterococcus* bacteria, *Klebsiella* bacteria, *Acinetobacter* bacteria, or a combination thereof.

Embodiment 28: A method for detecting a bacterial biofilm, the method comprisingcontacting an aqueous composition comprising a plurality of polymer nanoparticles comprising a copolymer comprising repeating units of formula (I) and (IX), wherein X is independently at each occurrence —O—, —S—, —CH$_2$—, —(CR$^4$R$^5$)—, or

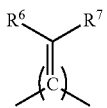

wherein R$^4$ and R$^5$ are independently at each occurrence a C$_{1-6}$ alkyl group and R$^6$ and R$^7$ are independently at each occurrence hydrogen or a C$_{1-6}$ alkyl group; L$^1$ is independently at each occurrence a divalent group that is (—CH$_2$—)$_z$, wherein z is an integer from 3 to 18; R$^1$ is independently at each occurrence an ammonium group, a phosphonium group, a zwitterionic group, a carboxylate group, a sulfonate group, an alkylene oxide group, or a combination thereof; Z is a divalent C$_{6-20}$ arylene group, a divalent C$_{1-20}$ alkylene oxide group, a divalent poly(C$_{1-6}$ alkylene oxide) group, or an amino acid containing group; y is 0 or 1; and R$^8$ is a fluorescent group; with a surface; and measuring fluorescence, wherein the presence of fluorescence is indicative of the presence of a bacterial biofilm.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

As used herein, the term "alkyl" means a branched or straight chain, saturated, monovalent hydrocarbon group, e.g., methyl, ethyl, i-propyl, and n-butyl. "Alkylene" means a straight or branched chain, saturated, divalent hydrocarbon group (e.g., methylene (—CH$_2$—) or propylene (—(CH$_2$)$_3$—)). "Aryl" means a monovalent, monocyclic or polycyclic aromatic group (e.g., phenyl or naphthyl). Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Groups that can be present on a substituted position include (—NO$_2$), cyano (—CN), hydroxy (—OH), halogen, thiol (—SH), thiocyano (—SCN), C$_{2-6}$ alkanoyl (e.g., acyl (H$_3$CC(=O)—); carboxamido; C$_{1-6}$ or C$_{1-3}$ alkyl, cycloalkyl, alkenyl, and alkynyl (including groups having at least one unsaturated linkages and from 2 to 8, or 2 to 6 carbon atoms); C$_{1-6}$ or C$_{1-3}$ alkoxy; C$_{6-10}$ aryloxy such as phenoxy; C$_{1-6}$ alkylthio; C$_{1-6}$ or C$_{1-3}$ alkylsulfinyl; C$_{1-6}$ or C$_{1-3}$ alkylsulfonyl; aminodi(C$_{1-6}$ or C$_{1-3}$)alkyl; C$_{6-12}$ aryl having at least one aromatic rings (e.g., phenyl, biphenyl, naphthyl, or the like, each ring either substituted or unsubstituted aromatic); C$_{7-19}$ arylalkyl having 1 to 3 separate or fused rings and from 6 to 18 ring carbon atoms; or arylalkoxy having 1 to 3 separate or fused rings and from 6 to 18 ring carbon atoms.

The invention claimed is:

1. An aqueous composition comprising a plurality of polymer nanoparticles, the polymer nanoparticles comprising, a polymer comprising repeating units of formula (I)

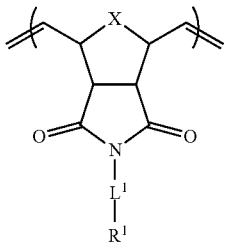
(I)

wherein
X is independently at each occurrence —O—, —S—, —CH$_2$—, —(CR$^4$R$^5$)—, or

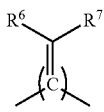

wherein R$^4$ and R$^5$ are independently at each occurrence a C$_{1-6}$ alkyl group and R$^6$ and R$^7$ are independently at each occurrence hydrogen or a C$_{1-6}$ alkyl group;

L$^1$ is independently at each occurrence a divalent group that is (—CH$_2$—)$_z$, wherein z is an integer from 8 to 18; and R$^1$ is independently at each occurrence an ammonium group, a phosphonium group, a zwitterionic group, a carboxylate group, a sulfonate group, an alkylene oxide group, or a combination thereof.

2. The aqueous composition of claim 1, wherein each nanoparticle of the plurality of nanoparticles has a diameter of 1 to 100 nanometers.

3. The aqueous composition of claim 1, wherein
X is —O— or —CH$_2$—;
z is an integer from 8 to 12; and
R$^1$ is an ammonium-containing group of formula (II)

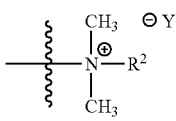
(II)

wherein
R$^2$ is a C$_{1-12}$ alkyl group or a C$_{7-20}$ alkylaryl group; and
Y is bromide, chloride, fluoride, iodide, hydroxide, phosphate, sulfonate, carbonate, acetate, hexafluorophosphate, tetrafluoroborate, mesylate, trifluoroacetate, p-toluenesulfonate, or a combination thereof.

4. The aqueous composition of claim 1, wherein
X is —O—;
z is an integer from 8 to 12; and
R$^1$ is an ammonium-containing group of formula (II)

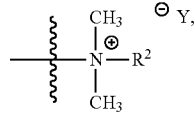
(II)

wherein R$^2$ is a C$_{1-6}$ alkyl group or a benzyl group and Y is bromide, hydroxide, or a combination thereof.

5. The aqueous composition of claim 1, wherein
X is —CH$_2$—;
z is an integer from 8 to 12; and
R$^1$ is an ammonium-containing group of formula (II)

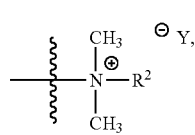
(II)

wherein R$^2$ is a C$_{1-10}$ alkyl group, and Y is bromide, hydroxide, or a combination thereof.

6. The aqueous composition of claim 1, wherein the polymer further comprises repeating units of formula (VIII)

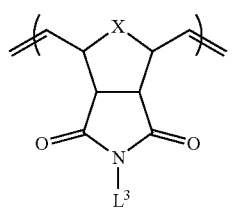
(VIII)

wherein
X is independently at each occurrence —O—, —S—, —CH$_2$—, —(CR$^4$R$^5$)—, or

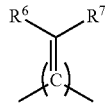

wherein R$^4$ and R$^5$ are independently at each occurrence a C$_{1-6}$ alkyl group and R$^6$ and R$^7$ are independently at each occurrence hydrogen or a C$_{1-6}$ alkyl group; and L$^3$ is independently at each occurrence a C$_{3-20}$ alkyl group.

7. The aqueous composition of claim 1, wherein the polymer further comprises repeating units of formula (IX)

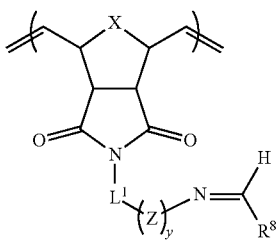

(IX)

wherein

X is independently at each occurrence —O—, —S—, —CH$_2$—, —(CR$^4$R$^5$)—, or

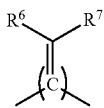

wherein R$^4$ and R$^5$ are independently at each occurrence a C$_{1-6}$ alkyl group and R$^6$ and R$^7$ are independently at each occurrence hydrogen or a C$_{1-6}$ alkyl group;

L$^1$ is independently at each occurrence a divalent group that is (—CH$_2$—)$_z$, wherein z is an integer from 8 to 18;

Z is a divalent C$_{6-20}$ arylene group, a divalent C$_{1-20}$ alkylene oxide group, a divalent poly (C$_{1-6}$ alkylene oxide) group, or an amino acid containing group;

y is 0 or 1; and

R$^8$ is a fluorescent group.

8. The aqueous composition of claim 7, wherein the repeating units of formula (IX) are present in a molar ratio of repeating units of formula (I):repeating units of formula (IX) of 15:1 to 5:1.

9. A method for detecting a bacterial biofilm, the method comprising:

contacting the aqueous composition comprising a plurality of polymer nanoparticles according to claim 7 with a surface; and measuring fluorescence, wherein the presence of fluorescence is indicative of the presence of a bacterial biofilm.

* * * * *